United States Patent
Yanagidate

(10) Patent No.: US 10,188,274 B2
(45) Date of Patent: Jan. 29, 2019

(54) CAPSULE ENDOSCOPE SYSTEM, CAPSULE ENDOSCOPE, RECEPTION APPARATUS, LIGHT EMISSION CONTROL METHOD OF CAPSULE ENDOSCOPE, AND COMPUTER READABLE STORAGE DEVICE

(71) Applicant: OLYMPUS CORPORATION, Tokyo (JP)

(72) Inventor: Masaharu Yanagidate, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 701 days.

(21) Appl. No.: 14/688,470

(22) Filed: Apr. 16, 2015

(65) Prior Publication Data
US 2015/0297066 A1 Oct. 22, 2015

(30) Foreign Application Priority Data

Apr. 18, 2014 (JP) .................. 2014-086431

(51) Int. Cl.
*A61B 1/04* (2006.01)
*A61B 1/00* (2006.01)
(Continued)

(52) U.S. Cl.
CPC .......... *A61B 1/041* (2013.01); *A61B 1/00006* (2013.01); *A61B 1/00009* (2013.01);
(Continued)

(58) Field of Classification Search
CPC . A61B 1/041; A61B 1/00006; A61B 1/00181; A61B 1/043; A61B 1/0638; A61B 1/0676; A61B 5/065; A61B 5/6861
(Continued)

(56) References Cited

U.S. PATENT DOCUMENTS 8,328,712 B2 * 12/2012 Nishiyama ......... A61B 1/00009
600/109
2003/0174208 A1 * 9/2003 Glukhovsky ...... A61B 1/00193
348/131
(Continued)

FOREIGN PATENT DOCUMENTS

| JP | 2006-068534 | 3/2006 |
| JP | 2009-178180 A | 8/2009 |
| JP | 5019589 | 9/2012 |

OTHER PUBLICATIONS

Notice of Reasons for Rejection Japanese Patent Application No. 2014-086431 dated Oct. 31, 2017 with English translation.

*Primary Examiner* — Timothy J Neal
*Assistant Examiner* — Jae Woo
(74) *Attorney, Agent, or Firm* — Pillsbury Winthrop Shaw Pittman, LLP

(57) ABSTRACT

A capsule endoscope or a reception apparatus executes a first light emission motion in which only a light emission module configured to perform light emission in an imaging direction of an imaging module that is performing imaging performs the light emission when no lesioned part is detected and executes a second light emission motion in which a light emission module configured to perform the light emission in a second imaging direction of an imaging module different from an imaging module that is imaging the lesioned part performs the light emission in synchronization with the light emission by a light emission module configured to perform the light emission in a first imaging direction of the imaging module that is imaging the lesioned part when the lesioned part is detected.

7 Claims, 12 Drawing Sheets

(51) Int. Cl.
*A61B 1/06* (2006.01)
*A61B 5/00* (2006.01)
*A61B 5/06* (2006.01)

(52) U.S. Cl.
CPC .......... *A61B 1/00181* (2013.01); *A61B 1/043* (2013.01); *A61B 1/0638* (2013.01); *A61B 1/0676* (2013.01); *A61B 5/0084* (2013.01); *A61B 5/065* (2013.01); *A61B 5/6861* (2013.01)

(58) Field of Classification Search
USPC .............................. 600/109, 103, 117, 118
See application file for complete search history.

(56) References Cited

U.S. PATENT DOCUMENTS

| | | | | |
|---|---|---|---|---|
| 2006/0106318 | A1* | 5/2006 | Davidson | A61B 1/04 600/476 |
| 2007/0165932 | A1* | 7/2007 | Nishimura | A61B 1/00016 382/128 |
| 2008/0039692 | A1* | 2/2008 | Hirakawa | A61B 1/00045 600/160 |
| 2008/0242926 | A1* | 10/2008 | Nishino | A61B 1/04 600/109 |
| 2009/0177033 | A1 | 7/2009 | Hendriks et al. | |
| 2009/0196476 | A1* | 8/2009 | Inoue | A61B 1/04 382/128 |
| 2015/0297067 | A1* | 10/2015 | Yanagidate | A61B 1/041 600/109 |
| 2017/0231470 | A1* | 8/2017 | Yanagidate | A61B 1/00016 600/118 |
| 2017/0245736 | A1* | 8/2017 | Mitsuhashi | A61B 1/00009 |

* cited by examiner

CAPSULE ENDOSCOPE SYSTEM, CAPSULE ENDOSCOPE, RECEPTION APPARATUS, LIGHT EMISSION CONTROL METHOD OF CAPSULE ENDOSCOPE, AND COMPUTER READABLE STORAGE DEVICE

BACKGROUND OF THE INVENTION

Field of the Invention

The present invention relates to technology of a capsule endoscope having a plurality of imaging modules.

Priority is claimed on Japanese Patent Application No. 2014-086431, filed Apr. 18, 2014, the entire content of which is hereby incorporated by reference.

Description of the Related Art

The diagnosis of a lesioned part or the like is performed using an image captured by a capsule endoscope inserted into a living body. In the publication of Japanese Unexamined Patent Application, First Publication No. 2006-68534, a method of performing imaging by alternately driving a plurality of imaging units in a capsule endoscope having the imaging units is disclosed. In addition, in the publication of Japanese Patent No. 5019589, a method of performing imaging by increasing an imaging rate of an imaging unit that images a lesioned part when the lesioned part has been found in a capsule endoscope having a plurality of imaging units is disclosed.

SUMMARY

According to a first aspect of the present invention, a capsule endoscope system includes: a capsule endoscope having: a first imaging module configured to direct an imaging direction in a first direction, image a first imaging range, and output first image data; a first light emission module configured to perform light emission in the first direction; a second imaging module configured to direct an imaging direction in a second direction different from the first direction, image a second imaging range that does not overlap the first imaging range at a second timing different from a first timing at which the first imaging module performs imaging, and output second image data; a second light emission module configured to perform light emission in the second direction; an imaging control unit configured to control the imaging of the first imaging module and the second imaging module; a light emission control unit configured to control light emissions of the first light emission module and the second light emission module; and a first wireless communication interface configured to transmit the first image data and the second image data; and a reception apparatus having a second wireless communication interface configured to receive the first image data and the second image data, wherein the capsule endoscope or the reception apparatus has: a lesioned part detection unit configured to detect a lesioned part from the first image data or the second image data; and a light emission motion instruction unit configured to instruct the light emission control unit to execute a first light emission motion in which only a light emission module configured to perform the light emission in the imaging direction of an imaging module that is performing imaging performs the light emission when no lesioned part is detected and instruct the light emission control unit to execute a second light emission motion in which a light emission module configured to perform the light emission in a second imaging direction of an imaging module different from an imaging module that is imaging the lesioned part performs the light emission in synchronization with the light emission by a light emission module configured to perform the light emission in a first imaging direction of the imaging module that is imaging the lesioned part when the lesioned part is detected.

According to a second aspect of the present invention, a capsule endoscope includes: a first imaging module configured to direct an imaging direction in a first direction, image a first imaging range, and output first image data; a first light emission module configured to perform light emission in the first direction; a second imaging module configured to direct an imaging direction in a second direction different from the first direction, image a second imaging range that does not overlap the first imaging range at a second timing different from a first timing at which the first imaging module performs imaging, and output second image data; a second light emission module configured to perform light emission in the second direction; an imaging control unit configured to control the imaging of the first imaging module and the second imaging module; a light emission control unit configured to control light emissions of the first light emission module and the second light emission module; a wireless communication interface configured to transmit the first image data and the second image data; a lesioned part detection unit configured to detect a lesioned part from the first image data or the second image data; and a light emission motion instruction unit configured to instruct the light emission control unit to execute a first light emission motion in which only a light emission module configured to perform the light emission in the imaging direction of an imaging module that is performing imaging performs the light emission when no lesioned part is detected and instruct the light emission control unit to execute a second light emission motion in which a light emission module configured to perform the light emission in a second imaging direction of an imaging module different from an imaging module that is imaging the lesioned part performs the light emission in synchronization with the light emission by a light emission module configured to perform the light emission in a first imaging direction of the imaging module that is imaging the lesioned part when the lesioned part is detected.

According to a third aspect of the present invention, a reception apparatus includes: a second wireless communication interface configured to receive first image data and second image data from a capsule endoscope having a first imaging module configured to direct an imaging direction in a first direction, image a first imaging range, and output the first image data; a first light emission module configured to perform light emission in the first direction; a second imaging module configured to direct an imaging direction in a second direction different from the first direction, image a second imaging range that does not overlap the first imaging range at a second timing different from a first timing at which the first imaging module performs imaging, and output second image data; a second light emission module configured to perform light emission in the second direction; an imaging control unit configured to control the imaging of the first imaging module and the second imaging module; a light emission control unit configured to control light emissions of the first light emission module and the second light emission module; and a first wireless communication interface configured to transmit the first image data and the second image data; a lesioned part detection unit configured to detect a lesioned part from the first image data or the second image data; and a light emission motion instruction unit configured to transmit instruction data for instructing the light emission control unit to execute a first light emission motion in which only a light emission module configured to perform the light emission in the imaging direction of an imaging module that is performing imaging performs the light emission when no lesioned part is detected and instructing the light emission control unit to execute a second light emission motion in which a light emission module configured to perform the light emission in a second imaging direction of an imaging module different from an imaging module that is imaging the lesioned part performs the light emission in synchronization with the light emission by a light emission module configured to perform the light emission in a first imaging direction of the imaging module that is imaging the lesioned part when the lesioned part is detected from the second wireless communication interface to the capsule endoscope.

According to a fourth aspect of the present invention, a light emission control method of a capsule endoscope comprising the steps of: detecting a lesioned part from first image data and second image data generated by the capsule endoscope having: a first imaging module configured to direct an imaging direction in a first direction, image a first imaging range, and output the first image data; a first light emission module configured to perform light emission in the first direction; a second imaging module configured to direct an imaging direction in a second direction different from the first direction, image a second imaging range that does not overlap the first imaging range at a second timing different from a first timing at which the first imaging module performs imaging, and output second image data; a second light emission module configured to perform light emission in the second direction; an imaging control unit configured to control the imaging of the first imaging module and the second imaging module; a light emission control unit configured to control light emissions of the first light emission module and the second light emission module; and a first wireless communication interface configured to transmit the first image data and the second image data; and instructing the light emission control unit to execute a first light emission motion in which only a light emission module configured to perform the light emission in the imaging direction of an imaging module that is performing imaging performs the light emission when no lesioned part is detected and instructing the light emission control unit to execute a second light emission motion in which a light emission module configured to perform the light emission in a second imaging direction of an imaging module different from an imaging module that is imaging the lesioned part performs the light emission in synchronization with the light emission by a light emission module configured to perform the light emission in a first imaging direction of the imaging module that is imaging the lesioned part when the lesioned part is detected.

According to a fifth aspect of the present invention, a computer readable storage device saves a computer program for causing a computer of a capsule endoscope to execute the steps of: detecting a lesioned part from first image data and second image data generated by the capsule endoscope having: a first imaging module configured to direct an imaging direction in a first direction, image a first imaging range, and output the first image data; a first light emission module configured to perform light emission in the first direction; a second imaging module configured to direct an imaging direction in a second direction different from the first direction, image a second imaging range that does not overlap the first imaging range at a second timing different from a first timing at which the first imaging module performs imaging, and output second image data; a second light emission module configured to perform light emission in the second direction; an imaging control unit configured to control the imaging of the first imaging module and the second imaging module; a light emission control unit configured to control light emissions of the first light emission module and the second light emission module; and a first wireless communication interface configured to transmit the first image data and the second image data; and instructing the light emission control unit to execute a first light emission motion in which only a light emission module configured to perform the light emission in the imaging direction of an imaging module that is performing imaging performs the light emission when no lesioned part is detected and instructing the light emission control unit to execute a second light emission motion in which a light emission module configured to perform the light emission in a second imaging direction of an imaging module different from an imaging module that is imaging the lesioned part performs the light emission in synchronization with the light emission by a light emission module configured to perform the light emission in a first imaging direction of the imaging module that is imaging the lesioned part when the lesioned part is detected.

According to a sixth aspect of the present invention, a computer readable storage device saves a computer program for causing a computer of a reception apparatus having a second wireless communication interface to execute the steps of: detecting a lesioned part from first image data and second image data generated by a capsule endoscope having: a first imaging module configured to direct an imaging direction in a first direction, image a first imaging range, and output the first image data; a first light emission module configured to perform light emission in the first direction; a second imaging module configured to direct an imaging direction in a second direction different from the first direction, image a second imaging range that does not overlap the first imaging range at a second timing different from a first timing at which the first imaging module performs imaging, and output second image data; a second light emission module configured to perform light emission in the second direction; an imaging control unit configured to control the imaging of the first imaging module and the second imaging module; a light emission control unit configured to control light emissions of the first light emission module and the second light emission module; and a first wireless communication interface configured to transmit the first image data and the second image data; and transmitting instruction data for instructing the light emission control unit to execute a first light emission motion in which only a light emission module configured to perform the light emission in the imaging direction of an imaging module that is performing imaging performs the light emission when no lesioned part is detected and instructing the light emission control unit to execute a second light emission motion in which a light emission module configured to perform the light emission in a second imaging direction of an imaging module different from an imaging module that is imaging the lesioned part performs the light emission in synchronization with the light emission by a light emission module configured to perform the light emission in a first imaging direction of the imaging module that is imaging the lesioned part when the lesioned part is detected from the second wireless communication interface, which receives the first image data and the second image data from the capsule endoscope, to the capsule endoscope.

DETAILED DESCRIPTION OF THE PREFERRED EMBODIMENTS

Hereinafter, embodiments of the present invention will be described with reference to the drawings.

First Embodiment

First, the first embodiment of the present invention will be described. In this embodiment, an example of a capsule endoscope system having a binocular capsule endoscope configured to wirelessly receive an instruction from a reception apparatus to execute switching of a light emission motion and transmit image data after imaging to the reception apparatus in wireless communication and the reception apparatus configured to receive the image data transmitted from the capsule endoscope and instruct the capsule endoscope to execute the light emission motion according to a result of determining whether there is a lesioned part from the image data will be described.

In the capsule endoscope according to this embodiment, each imaging module alternately performs imaging. When the lesioned part is not found, the capsule endoscope executes a normal light emission motion in which only the light emission module configured to emit light in an imaging direction of the imaging module that is performing imaging performs the light emission motion. In addition, when the lesioned part is found, the capsule endoscope executes a lesion light emission motion in which a light emission module configured to perform the light emission in a second imaging direction of an imaging module different from an imaging module that is imaging the lesioned part performs the light emission in synchronization with the light emission by a light emission module configured to perform the light emission in the first imaging direction of the imaging module that is imaging the lesioned part.

(System Configuration)

Figure 1:
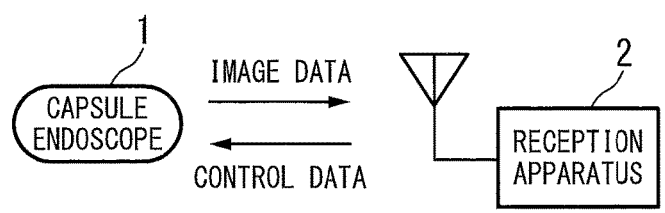
FIG. 1 is a block diagram illustrating a configuration example of a capsule endoscope system according to a first embodiment of the present invention.
Figure 2:
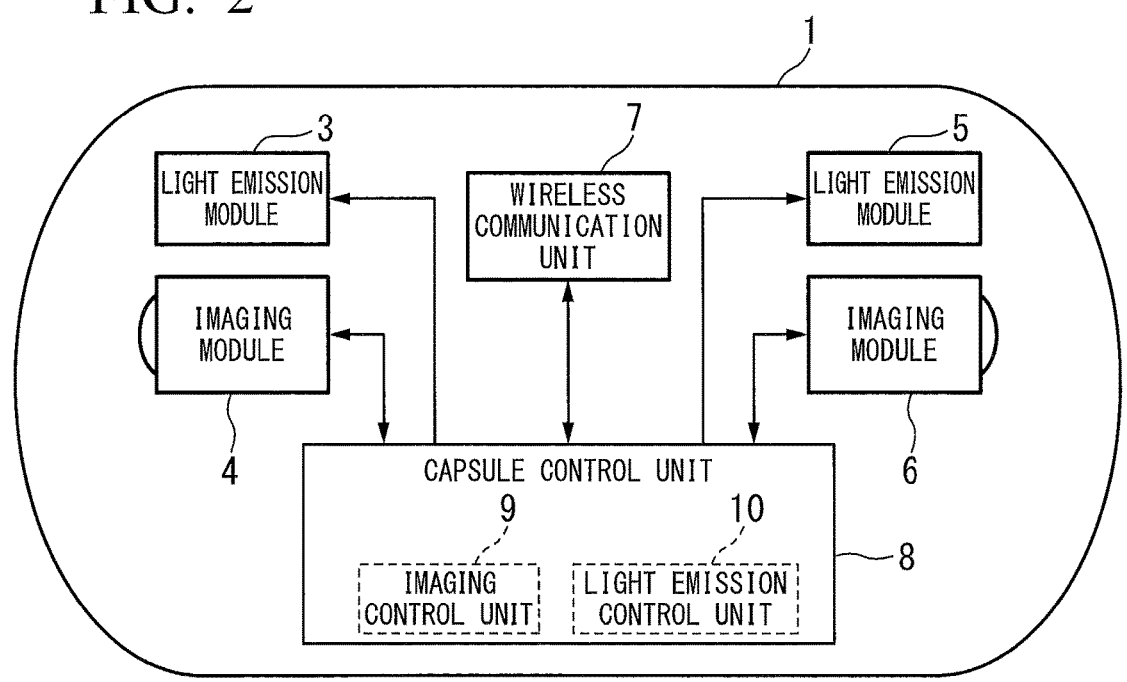
FIG. 2 is a block diagram illustrating a configuration example of a capsule endoscope according to the first embodiment of the present invention.
Figure 3:
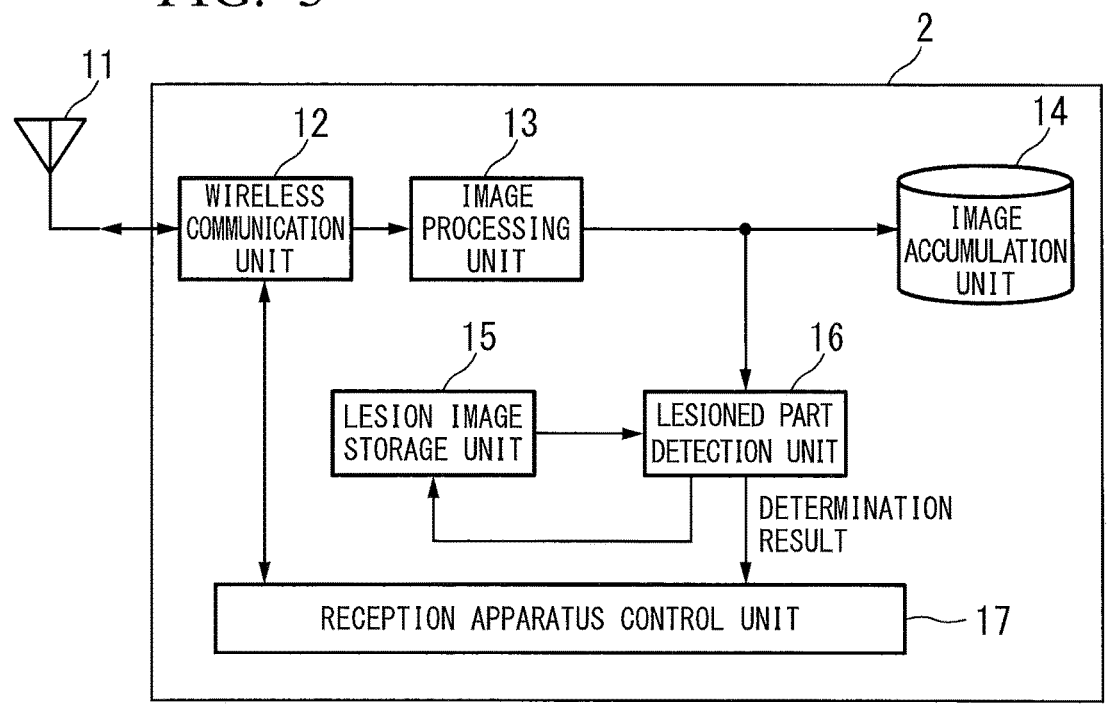
FIG. 3 is a block diagram illustrating a configuration example of a reception apparatus according to the first embodiment of the present invention.
Figure 4:
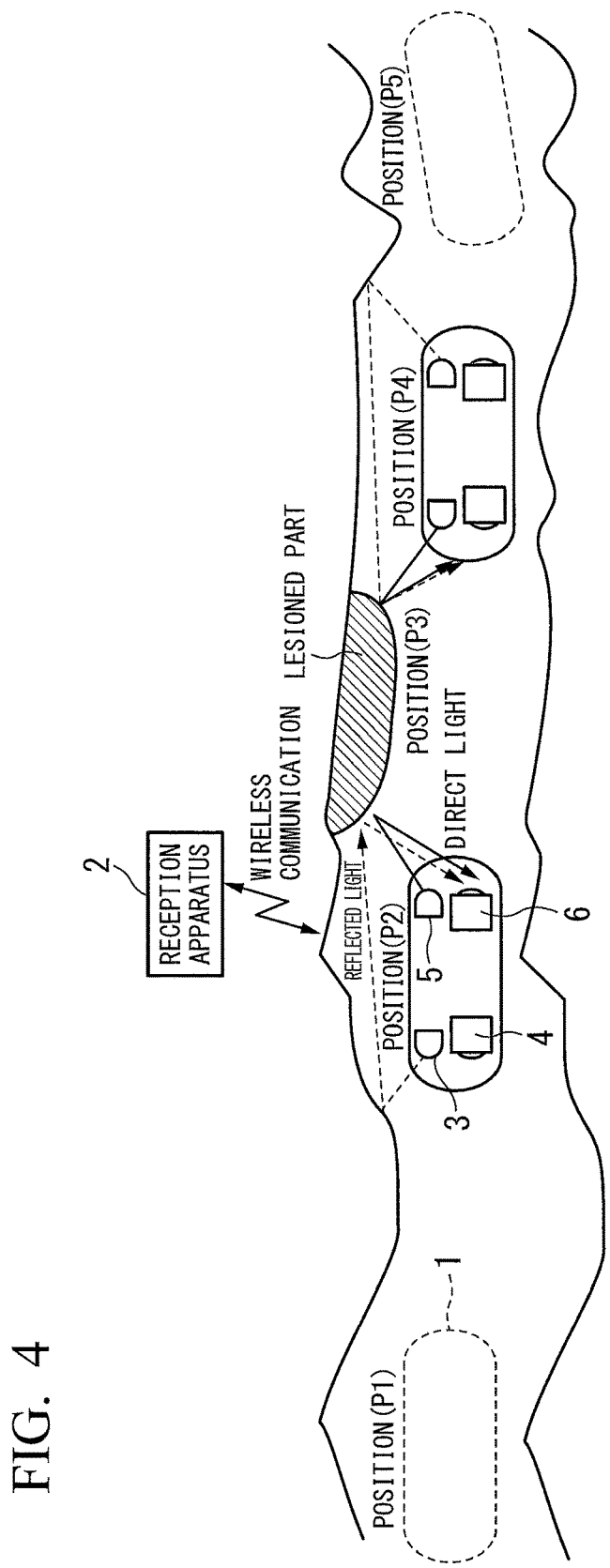
FIG. 4 is a reference diagram illustrating a state of a light emission motion for the capsule endoscope to illuminate a lesioned part according to the first embodiment of the present invention.
Figure 5:
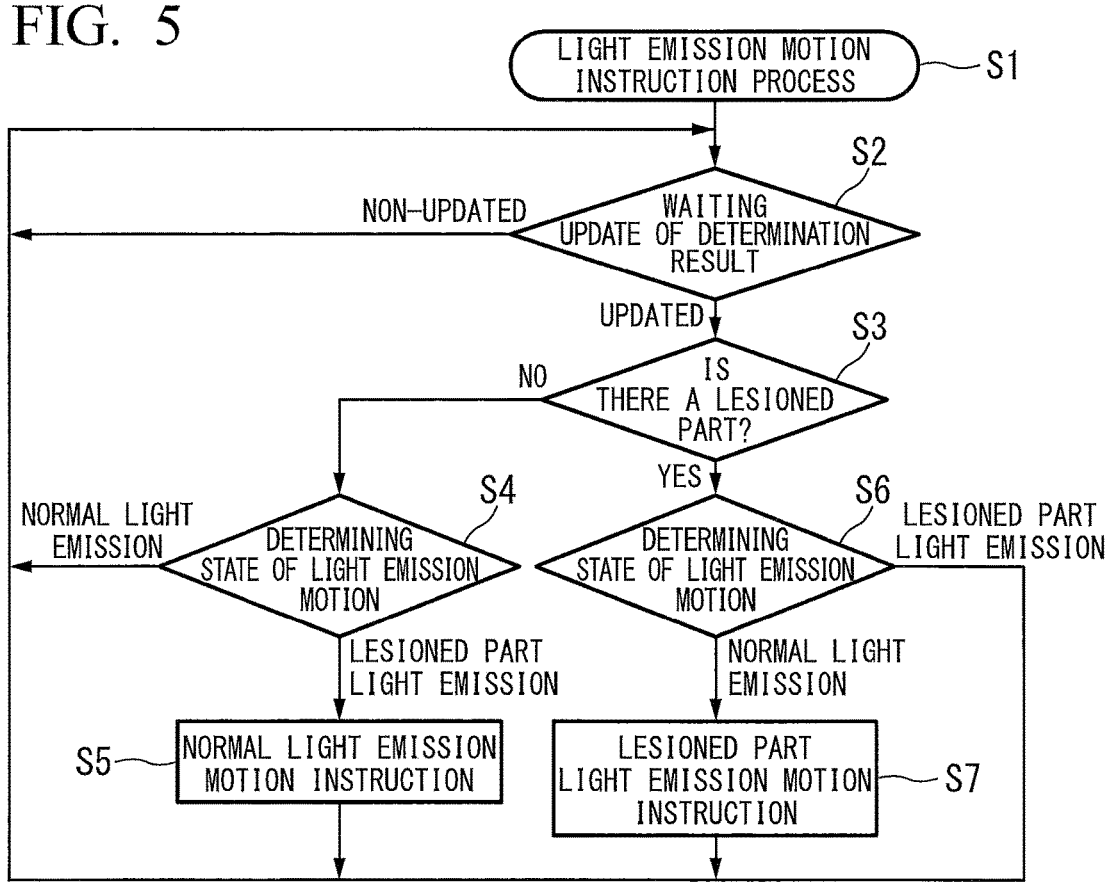
FIG. 5 is a flowchart illustrating a procedure of a light emission motion instruction process performed by the reception apparatus according to the first embodiment of the present invention.

Configurations of the capsule endoscope system, the capsule endoscope 1, and the reception apparatus 2 and operations of the capsule endoscope 1 and the reception apparatus 2 will be described using FIGS. 1 to 5. FIG. 1 is a block diagram illustrating a configuration example of the capsule endoscope system according to this embodiment. FIG. 2 is a block diagram illustrating a configuration example of the capsule endoscope 1 according to this embodiment. FIG. 3 is a block diagram illustrating a configuration example of the reception apparatus 2 according to this embodiment. FIG. 4 is a reference diagram illustrating a state of a light emission motion for the capsule endoscope 1 to illuminate a lesioned part according to this embodiment. FIG. 5 is a flowchart illustrating a procedure of a light emission motion instruction process performed by the reception apparatus 2 according to this embodiment.

As illustrated in FIG. 1, the capsule endoscope system of this embodiment has the capsule endoscope 1 and the reception apparatus 2. The capsule endoscope 1 and the reception apparatus 2 are connected by wireless communication. The capsule endoscope 1 is inserted into a living body (human body) and image data obtained through imaging is wirelessly transmitted. The wirelessly transmitted image data is received by an antenna within the reception apparatus 2. A reception process is performed on the received image data. The reception apparatus 2 stores the received image data and controls a light emission state of the capsule endoscope 1 by wirelessly transmitting control data (various types of instruction data to be described below) for controlling a light emission motion of the capsule endoscope 1.

The capsule endoscope 1 has two imaging modules. As illustrated in FIG. 2, the imaging modules perform imaging in mutually opposite directions. When the lesioned part is found from the image data received from the capsule endoscope 1, the reception apparatus 2 instructs the capsule endoscope 1 to perform the lesion light emission motion. In addition, when the capsule endoscope 1 is separated from the lesioned part after the lesioned part is imaged and the lesioned part is not found from the image data, the reception apparatus 2 instructs the capsule endoscope 1 to perform the normal light emission motion. Because a configuration of the capsule endoscope system other than the configuration related to light emission control of the capsule endoscope 1 is well known, detailed description thereof will be omitted.

(Configuration/Operation of Each Apparatus)

As illustrated in FIG. 2, the capsule endoscope 1 has a light emission module 3, an imaging module 4, a light emission module 5, an imaging module 6, a wireless communication unit 7, and a capsule control unit 8.

The light emission module 3, the imaging module 4, the light emission module 5, and the imaging module 6 cooperatively perform illumination and imaging processes. The imaging modules 4 and 6 are modules configured to perform the imaging process and output image data and have a lens and an imaging element. Because an imaging module for the capsule endoscope is well known, description thereof will be omitted.

The imaging modules 4 and 6 are disposed on both ends (a first end and a second end different from the first end) of a main body of the capsule endoscope 1 so that imaging surfaces of the imaging modules 4 and 6 turn their backs to each other. The imaging module 4 is disposed on the first end of the capsule endoscope 1 so that an imaging direction becomes an outward direction. The imaging module 6 is disposed so that the imaging direction is an outward direction, that is, a direction which is substantially opposite to the imaging direction of the imaging module 4, on the second end of the capsule endoscope 1. In addition, the imaging modules 4 and 6 are disposed so that the imaging directions are substantially the same as a moving direction or a backward direction of the capsule endoscope 1. A unital external shape of the capsule endoscope 1 has two straight lines which are substantially parallel and two curves which are opposed. The imaging modules 4 and 6 are disposed so that the imaging directions are substantially parallel to the two straight lines.

One of the imaging modules 4 and 6 serves as a first imaging module configured to direct an imaging direction in a first direction, image a first imaging range, and output the first image data, and the other serves as a second imaging module configured to direct an imaging direction in a second direction different from the first direction, image a second imaging range that does not overlap the first imaging range at a second timing different from a first timing at which the first imaging module performs imaging, and output second image data. In addition, one of the imaging modules 4 and 6 serves as an imaging module having the imaging direction closer to the moving direction (or the imaging direction which is substantially the same as the moving direction), and the other serves as an imaging module having the imaging direction farther from the moving direction (or the imaging direction which is substantially opposite to the moving direction). If the imaging direction is closer to the moving direction, this means that an angle formed by the imaging direction and the moving direction is relatively small. In addition, if the imaging direction is farther from the moving direction, this means that the angle formed by the imaging direction and the moving direction is relatively large.

In either of the normal light emission motion and the lesion light emission motion, the imaging modules 4 and 6 alternately perform imaging. That is, the imaging module 4 performs imaging during a non-imaging time of the imaging module 6 and the imaging module 6 performs imaging during a non-imaging time of the imaging module 4.

The light emission modules 3 and 5 are modules configured to illuminate imaging ranges of the imaging modules 4 and 6 and have a light emission diode (LED) element and a buffer for driving the LED element. One of the light emission modules 3 and 5 serves as a first light emission module configured to perform light emission in a first direction, and the other serves as a second light emission module configured to perform light emission in a second direction. The light emission module 3 performs the light emission in the imaging direction of the imaging module 4 and the light emission module 5 performs the light emission in the imaging direction of the imaging module 6. Because the light emission module for the capsule endoscope is well known, description thereof will be omitted.

The wireless communication unit 7 performs wireless communication with the reception apparatus 2. The wireless communication unit 7 is a first wireless communication interface configured to transmit image data output from the imaging module 4 and the imaging module 6 to the reception apparatus 2 and receive instruction data for controlling the imaging motions of the imaging module 4 and the imaging module 6 from the reception apparatus 2. Image data output from the imaging modules 4 and 6 is input to the capsule control unit 8 and converted into communication data by the capsule control unit 8. This data is wirelessly transmitted to the reception apparatus 2 via the wireless communication unit 7.

The capsule control unit 8 controls each unit within the capsule endoscope 1. The capsule control unit 8 has an imaging control unit 9 and a light emission control unit 10. The imaging control unit 9 controls imaging of the imaging modules 4 and 6. The light emission control unit 10 controls light emissions of the light emission modules 3 and 5. When instruction data is received by the wireless communication unit 7, the light emission control unit 10 controls the light emissions of the light emission modules 3 and 5 based on the instruction data.

In addition, the capsule control unit 8 stores a program and necessary data for controlling an operation of the capsule control unit 8. A function of the capsule control unit 8, for example, can be implemented as a function of software by causing a computer of the capsule endoscope 1 to read and execute a program including a command for prescribing the operation of the capsule control unit 8. In addition, this program, for example, may be provided by a "computer-readable recording medium" such as a flash memory. In addition, the above-described program may be input to the capsule endoscope 1 when the program is transmitted from a computer in which the program is stored in a storage apparatus or the like to the capsule endoscope 1 via a transmission medium or through transmission waves of the transmission medium. Here, the "transmission medium" for transmitting the program includes a medium having a function of transmitting information, such as a network (communication network) like the Internet or a communication circuit (communication line) like a telephone circuit. In addition, the above-described program may implement some of the above-described functions. Further, the above-described program may be a program, i.e., a so-called differential file (differential program), capable of implementing the above-described function in combination with a program already recorded on the computer system.

As illustrated in FIG. 3, the reception apparatus 2 has an antenna 11, a wireless communication unit 12, an image processing unit 13, an image accumulation unit 14, a lesion image storage unit 15, a lesioned part detection unit 16, and a reception apparatus control unit 17.

The wireless communication unit 12 performs wireless communication with the capsule endoscope 1 via the antenna 11. The wireless communication unit 12 is a second wireless communication interface configured to receive image data from the capsule endoscope 1 and transmit instruction data to the capsule endoscope 1. The image processing unit 13 performs image processing such as color conversion on the image data received by the wireless communication unit 12. The image data processed by the image processing unit 13 is output to the image accumulation unit 14 and the lesioned part detection unit 16. The image accumulation unit 14 is a storage module configured to accumulate image data processed by the image processing unit 13 for a plurality of frames in units of frames.

The lesion image storage unit 15 is a storage module configured to store lesion image data which is image data of a lesioned part. Various types of lesion image data stored in the lesion image storage unit 15 is appropriately read by an instruction from the lesioned part detection unit 16 according to the progress of a process of detecting the lesioned part.

The lesioned part detection unit 16 compares the image data output from the image processing unit 13 to various types of lesion image data stored in the lesion image storage unit 15, and determines whether there is a lesioned part in the image data output from the image processing unit 13. That is, the lesioned part detection unit 16 detects the lesioned part from the image data output from the imaging module 4 or 6 of the capsule endoscope 1. A process of determining whether there is a lesioned part in the image data using the lesion image data is performed by a determination algorithm such as pattern matching. Because the determination algorithm is well known, detailed description thereof will be omitted. Determination result data indicating a result of the determination made by the lesioned part detection unit 16 is output to the reception apparatus control unit 17. In addition, when it is determined that the lesioned part is present, the lesioned part detection unit 16 can output the image data in which the lesioned part is determined to be present to the lesion image storage unit 15 and the lesion image storage unit 15 can store the image data.

The reception apparatus control unit 17 controls each unit within the reception apparatus 2. In addition, the reception apparatus control unit 17 performs control to be described below. The reception apparatus control unit 17 instructs the light emission control unit 10 of the capsule endoscope 1 to execute a first light emission motion, that is, a normal light emission motion, in which only a light emission module configured to perform the light emission in the imaging direction of an imaging module that is performing imaging performs the light emission when no lesioned part is detected and instructs the light emission control unit 10 to execute a second light emission motion, that is, a lesion light emission motion, in which a light emission module configured to perform the light emission in a second imaging direction of an imaging module different from an imaging module that is imaging the lesioned part performs the light emission in synchronization with the light emission by a light emission module configured to perform the light emission in a first imaging direction of the imaging module that is imaging the lesioned part when the lesioned part is detected.

In the normal light emission motion, one light emission module performs the light emission in synchronization with imaging by the imaging module during the imaging. That is, one light emission module performs the light emission within a period (one frame period) in which the imaging module performs the imaging. For example, one light emission module performs the light emission substantially simultaneously with the imaging by the imaging module that is performing the imaging.

In the lesion light emission motion, two light emission modules perform light emissions in synchronization with the imaging by the imaging module that is imaging the lesioned part. That is, within the period in which the imaging module that is imaging the lesioned part performs the imaging, the light emission module configured to perform the light emission in a first imaging direction and the light emission module configured to perform the light emission in a second imaging direction perform the light emissions. For example, within the period in which the imaging module that is imaging the lesioned part performs the imaging, the light emission module configured to perform the light emission in the second imaging direction performs the light emission substantially simultaneously with the light emission by the light emission module configured to perform the light emission in the first imaging direction. Within the period in which the imaging module that is imaging the lesioned part performs the imaging, the light emission by the light emission module configured to perform the light emission in the first imaging direction and the light emission by the light emission module configured to perform the light emission in the second imaging direction may be sequentially performed.

In the lesion light emission motion, the light emission module configured to perform the light emission in the second imaging direction of the imaging module different from an imaging module that is imaging the lesioned part performs the light emission in synchronization with the light emission by the other light emission module as described above and performs the light emission in synchronization with the imaging by the imaging module different from the imaging module that is imaging the lesioned part. That is, in the lesion light emission motion, the reception apparatus control unit 17 instructs the light emission control unit 10 to execute an operation in which the light emission modules 3 and 5 perform the light emissions during the imaging by the imaging modules corresponding thereto and the above-described lesion light emission motion.

The reception apparatus control unit 17 generates instruction data indicating an instruction of the normal light emission motion or the lesion light emission motion and transmits instruction data from the wireless communication unit 12 to the capsule endoscope 1. After the transmitted instruction data is received by the wireless communication unit 7 of the capsule endoscope 1, the instruction data is output to the capsule control unit 8 and used in light emission control.

In addition, the reception apparatus control unit 17 stores a program or necessary data for controlling an operation of the reception apparatus control unit 17. A process of implementing a function of the lesioned part detection unit 16 may be performed by the reception apparatus control unit 17. A function of the reception apparatus control unit 17, for example, can be implemented as a function of software by causing a computer of the reception apparatus 2 to read and execute a program including a command for prescribing the operation of the reception apparatus control unit 17. A method of installing the program may be similar to a method of installing a program for controlling the operation of the capsule control unit 8 of the capsule endoscope 1.

(Specific Operation of Light Emission Control)

Detailed content of the light emission motion will be described using FIGS. 4 and 5. FIG. 4 illustrates a change in the light emission motion when the capsule endoscope 1 passes through the lesioned part based on a position of the capsule endoscope 1. In FIG. 4, the capsule endoscope 1 moves from the left to the right.

In this embodiment, an example in which the capsule endoscope 1 sequentially reaches positions P4 and P5 by passing through a position P2 from a position P1 and passing through a position P3 of the lesioned part as illustrated in FIG. 4 will be described. It is difficult to find the lesioned part between the positions P1 and P2 and between the positions P4 and P5. The lesioned part is found in image data output from the imaging module 6 between the positions P2 and P3, and the lesioned part is found in image data output from the imaging module 4 between the positions P3 and P4.

The lesioned part is detected from image data obtained through imaging by the imaging module 6 at the position P2. Thus, the reception apparatus control unit 17 transmits instruction data for instructing to execute the lesion light emission motion corresponding to the imaging module 6 from the wireless communication unit 12 to the capsule endoscope 1. Upon receiving the instruction data for instructing to execute the lesion light emission motion corresponding to the imaging module 6, the capsule endoscope 1 sets execution content of the lesion light emission motion corresponding to the imaging module 6 in the light emission control unit 10.

As described above, the lesion light emission motion is an operation in which a light emission module configured to perform the light emission in a second imaging direction of an imaging module different from an imaging module that is imaging the lesioned part performs the light emission in synchronization with the light emission by a light emission module configured to perform the light emission in the first imaging direction of the imaging module that is imaging the lesioned part. Thus, in the lesion light emission motion corresponding to the imaging module 6, the light emission modules 3 and 5 simultaneously perform the light emissions in synchronization with the imaging timing of the imaging module 6.

As illustrated in FIG. 4, when the lesion light emission motion corresponding to the imaging module 6 is performed at the position P2, illumination by reflected light from the light emission module 3, as well as illumination by direct light from the light emission module 5, is performed. Thus, an illumination state of the lesioned part is improved and a clearer image of the lesioned part can be obtained.

When the capsule endoscope 1 comes to the position P3 of the lesioned part, the lesioned part is detected from both image data output from the imaging module 4 and image data output from the imaging module 6. Thus, the lesion light emission motion corresponding to the imaging module 4 and the lesion light emission motion corresponding to the imaging module 6 are performed in parallel.

In this case, although the imaging motions of the imaging modules 4 and 6 are alternately performed, the light emission modules 3 and 5 perform the light emissions at any imaging motion time. At the position P3, the light emission modules 3 and 5 perform the normal light emission motions when no lesioned part is detected from image data of either of the image data output from the imaging module 4 and the image data output from the imaging module 6.

When the capsule endoscope 1 passes the position P3 of the lesioned part, the lesioned part is detected from the image data output from the imaging module 4. Thus, the reception apparatus control unit 17 transmits instruction data for instructing to execute the lesion light emission motion corresponding to the imaging module 4 from the wireless communication unit 12 to the capsule endoscope 1.

In the lesion light emission motion corresponding to the imaging module 4, the light emission modules 3 and 5 simultaneously perform the light emissions in synchronization with the imaging by the imaging module 4. As illustrated in FIG. 4, when the lesion light emission motion corresponding to the imaging module 4 is performed at the position P4, illumination by reflected light from the light emission module 5, as well as illumination by direct light from the light emission module 3, is performed. Thus, an illumination state of the lesioned part is improved and a clearer image of the lesioned part can be obtained.

FIG. 5 illustrates a procedure of a light emission motion instruction process S1 performed by the reception apparatus control unit 17. The reception apparatus control unit 17 instructs to execute the light emissions to be performed by the light emission modules 3 and 5 based on a determination result related to whether there is a lesioned part output from the lesioned part detection unit 16.

Types of light emission motions in this embodiment include four types of the normal light emission motion corresponding to the imaging module 4, the lesion light emission motion corresponding to the imaging module 4, the normal light emission motion corresponding to the imaging module 6, and the lesion light emission motion corresponding to the imaging module 6. The light emission motion instruction process S1 is a process of determining the light emission motion for every imaging module according to whether the lesioned part is included in the image data output from each imaging module. For example, according to whether the lesioned part is included in the image data output from the imaging module 4, one of the normal light emission motion corresponding to the imaging module 4 and the lesion light emission motion corresponding to the imaging module 4 is selected.

The reception apparatus control unit 17 recognizes which of the imaging modules 4 and 6 outputs image data used in the detection of the lesioned part by the lesioned part detection unit 16. The reception apparatus control unit 17 determines the light emission motion according to which imaging module has output the image data used in the detection of the lesioned part by the lesioned part detection unit 16 and whether the lesioned part is included in the image data.

The following process is performed in the light emission motion instruction process S1. First, the reception apparatus control unit 17 performs determination result update waiting S2 for waiting for the update of the determination result output from the lesioned part detection unit 16. When the reception apparatus control unit 17 has the function of the lesioned part detection unit 16, the reception apparatus control unit 17 performs a process of detecting the lesioned part from the image data in place of the determination result update waiting S2.

After the determination result is updated, the reception apparatus control unit 17 makes a determination of whether the lesioned part is present based on the determination result (S3). When the determination result output from the lesioned part detection unit 16 indicates that there is a lesioned part, it is determined that the lesioned part is present. In addition, when the determination result output from the lesioned part detection unit 16 indicates that there is no lesioned part, it is determined that the lesioned part is absent.

When it is determined that the lesioned part is absent, the reception apparatus control unit 17 makes a light emission motion state determination S4 for determining a state of the light emission motion corresponding to the imaging module outputting the image data used in the detection of the lesioned part. The reception apparatus control unit 17 stores information indicating a current state of the light emission motion and makes a determination based on the information. When the state of the light emission motion is the normal light emission motion, the determination result update waiting S2 is performed.

When the state of the light emission motion is the lesion light emission motion, the reception apparatus control unit 17 performs a normal light emission motion instruction (S5) for instructing the capsule endoscope 1 to perform the normal light emission motion. In the normal light emission motion instruction S5, the reception apparatus control unit 17 generates instruction data indicating the instruction of the normal light emission motion and transmits the instruction data from the wireless communication unit 12 to the capsule endoscope 1. The capsule control unit 8 of the capsule endoscope 1 instructs the light emission control unit 10 to execute the normal light emission motion based on the instruction data received by the wireless communication unit 7. The light emission control unit 10 causes the light emission modules 3 and 5 to start the normal light emission motion. When the normal light emission motion instruction S5 is performed, the information indicating the current state of the light emission motion stored by the reception apparatus control unit 17 is updated to a value indicating the normal light emission motion. After the normal light emission motion instruction S5, the determination result update waiting S2 is performed.

When it is determined that the lesioned part is present in the determination S3 of whether the lesioned part is present, the reception apparatus control unit 17 makes a light emission motion state determination S6 for determining the state of the light emission motion corresponding to the imaging module outputting image data used in the detection of the lesioned part. As described above, the reception apparatus control unit 17 makes the determination based on the information indicating the current state of the light emission motion. When the state of the light emission motion is the lesion light emission motion, the determination result update waiting S2 is performed.

When the state of the light emission motion is the normal light emission motion, the reception apparatus control unit 17 performs a lesion light emission motion instruction S7 for instructing the capsule endoscope 1 to perform the lesion light emission motion. In the lesion light emission motion instruction S7, the reception apparatus control unit 17 generates instruction data indicating the instruction of the lesion light emission motion and transmits the instruction data from the wireless communication unit 12 to the capsule endoscope 1. Information indicating the imaging module outputting the image data from which the lesioned part is detected, that is, the imaging module that is imaging the lesioned part, is included in the instruction data. The capsule control unit 8 of the capsule endoscope 1 instructs the light emission control unit 10 to execute the lesion light emission motion based on the instruction data received by the wireless communication unit 7. The light emission control unit 10 causes the light emission modules 3 and 5 to start the lesion light emission motion in which the other light emission module performs the light emission in synchronization with the light emission by a light emission module configured to perform the light emission in the imaging direction of the imaging module indicated by the information included in the instruction data. When the lesion light emission motion instruction S7 is performed, the information indicating the current state of the light emission motion stored by the reception apparatus control unit 17 is updated to a value indicating the lesion light emission motion. After the lesion light emission motion instruction S7, the determination result update waiting S2 is performed.

In this embodiment, the image processing unit 13 and the image accumulation unit 14 are not essential components for obtaining a characteristic effect of the capsule endoscope system according to this embodiment. In addition, the lesion image storage unit 15, for example, may be a storage module provided in an apparatus on a network and the reception apparatus 2 may acquire the lesion image data from the apparatus through communication. Accordingly, the lesion image storage unit 15 is not an essential component in the capsule endoscope system according to this embodiment.

According to this embodiment, a capsule endoscope system is configured to include: the capsule endoscope 1 having a first imaging module (imaging module 4 or 6) configured to direct an imaging direction in a first direction, image a first imaging range, and output first image data; a first light emission module (light emission module 3 or 5) configured to perform light emission in the first direction; a second imaging module (imaging module 4 or 6) configured to direct an imaging direction in a second direction different from the first direction, image a second imaging range that does not overlap the first imaging range at a second timing different from a first timing at which the first imaging module performs imaging, and output second image data; a second light emission module (light emission module 3 or 5) configured to perform light emission in the second direction; the imaging control unit 9 configured to control the imaging of the first imaging module and the second imaging module; the light emission control unit 10 configured to control light emissions of the first light emission module and the second light emission module; and a first wireless communication interface (wireless communication unit 7) configured to transmit the first image data and the second image data; and the reception apparatus 2 having a second wireless communication interface (wireless communication unit 12) configured to receive the first image data and the second image data, wherein the reception apparatus 2 has the lesioned part detection unit 16 configured to detect a lesioned part from the first image data or the second image data; and a light emission motion instruction unit (reception apparatus control unit 17) configured to instruct the light emission control unit 10 to execute a first light emission motion in which only a light emission module configured to perform the light emission in the imaging direction of an imaging module that is performing imaging performs the light emission when no lesioned part is detected and instruct the light emission control unit 10 to execute a second light emission motion in which a light emission module configured to perform the light emission in a second imaging direction of an imaging module different from an imaging module that is imaging the lesioned part performs the light emission in synchronization with the light emission by a light emission module configured to perform the light emission in a first imaging direction of the imaging module that is imaging the lesioned part when the lesioned part is detected.

In addition, according to this embodiment, the reception apparatus 2 is configured to include a second wireless communication interface (wireless communication unit 12) configured to receive first image data and second image data from the capsule endoscope 1; the lesioned part detection unit 16 configured to detect a lesioned part from the first image data or the second image data; and a light emission motion instruction unit (reception apparatus control unit 17) configured to transmit instruction data for instructing the light emission control unit 10 to execute a first light emission motion in which only a light emission module configured to perform the light emission in the imaging direction of an imaging module that is performing imaging performs the light emission when no lesioned part is detected and instructing the light emission control unit 10 to execute a second light emission motion in which a light emission module configured to perform the light emission in a second imaging direction of an imaging module different from an imaging module that is imaging the lesioned part performs the light emission in synchronization with the light emission by a light emission module configured to perform the light emission in a first imaging direction of the imaging module that is imaging the lesioned part when the lesioned part is detected from the second wireless communication interface to the capsule endoscope 1.

In addition, according to this embodiment, a light emission control method of the capsule endoscope is configured to include the step S3 of detecting a lesioned part from first image data or second image data generated by the capsule endoscope 1; and the steps S5 and S7 of instructing the light emission control unit 10 to execute a first light emission motion in which only a light emission module configured to perform the light emission in the imaging direction of an imaging module that is performing imaging performs the light emission when no lesioned part is detected and instructing the light emission control unit 10 to execute a second light emission motion in which a light emission module configured to perform the light emission in a second imaging direction of an imaging module different from an imaging module that is imaging the lesioned part performs the light emission in synchronization with the light emission by a light emission module configured to perform the light emission in the first imaging direction of the imaging module that is imaging the lesioned part when the lesioned part is detected.

In addition, according to this embodiment, a program is configured to cause a computer of the reception apparatus 2 having a second wireless communication interface to execute the step S3 of detecting a lesioned part from first image data or second image data generated by the capsule endoscope 1; and the steps S5 and S7 of transmitting instruction data for instructing the light emission control unit 10 to execute a first light emission motion in which only a light emission module configured to perform the light emission in the imaging direction of an imaging module that is performing imaging performs the light emission when no lesioned part is detected and instructing the light emission control unit 10 to execute a second light emission motion in which a light emission module configured to perform the light emission in a second imaging direction of an imaging module different from an imaging module that is imaging the lesioned part performs the light emission in synchronization with the light emission by a light emission module configured to perform the light emission in the first imaging direction of the imaging module that is imaging the lesioned part when the lesioned part is detected from the second wireless communication interface (wireless communication unit 12), which receives the first image data and the second image data from the capsule endoscope 1, to the capsule endoscope 1.

In this embodiment, it is possible to obtain a clearer image of a lesioned part by instructing the light emission control unit 10 to execute a first light emission motion, that is, the normal light emission motion, in which only the light emission module configured to perform the light emission in the imaging direction of an imaging module that is performing imaging performs the light emission when no lesioned part is detected and instructing the light emission control unit 10 to execute a second light emission motion, that is, the lesion light emission motion, in which a light emission module configured to perform the light emission in a second imaging direction of an imaging module different from an imaging module that is imaging the lesioned part performs the light emission in synchronization with the light emission by a light emission module configured to perform the light emission in the first imaging direction of the imaging module that is imaging the lesioned part when the lesioned part is detected.

Second Embodiment

Next, the second embodiment of the present invention will be described. This embodiment is an example in which a capsule endoscope performs a process of detecting a lesioned part from image data and a process of instructing to execute a light emission motion as the processes performed by the reception apparatus in the first embodiment. In this embodiment, the capsule endoscope 1 in the first embodiment is changed to a capsule endoscope 20 illustrated in FIG. 6.

Figure 6:
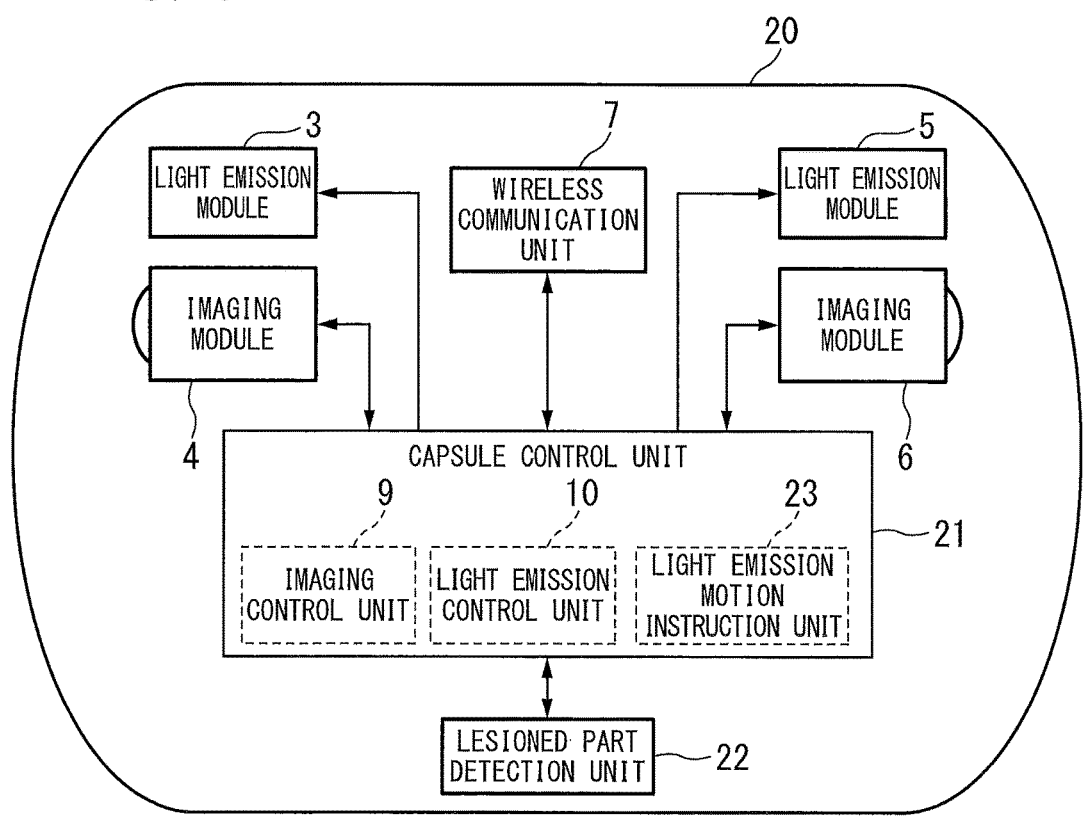
FIG. 6 is a block diagram illustrating a configuration example of a capsule endoscope according to a second embodiment of the present invention.

FIG. 6 illustrates a configuration example of the capsule endoscope 20. As illustrated in FIG. 6, the capsule endoscope 20 has a light emission module 3, an imaging module 4, a light emission module 5, an imaging module 6, a wireless communication unit 7, a capsule control unit 21, and a lesioned part detection unit 22. In the capsule endoscope 20 of this embodiment, the capsule control unit 8 in the capsule endoscope 1 illustrated in FIG. 2 is changed to the capsule control unit 21 and the lesioned part detection unit 22 is added.

The capsule control unit 21 has an imaging control unit 9, a light emission control unit 10, and a light emission motion instruction unit 23. Because the imaging control unit 9 and the light emission control unit 10 have been described in the first embodiment, description thereof will be omitted. The light emission motion instruction unit 23 instructs the light emission control unit 10 to execute a first light emission motion, that is, a normal light emission motion, in which only a light emission module configured to perform the light emission in the imaging direction of an imaging module that is performing imaging performs the light emission when no lesioned part is detected and instructs the light emission control unit 10 to execute a second light emission motion, that is, a lesion light emission motion, in which a light emission module configured to perform the light emission in a second imaging direction of an imaging module different from an imaging module that is imaging the lesioned part performs the light emission in synchronization with the light emission by a light emission module configured to perform the light emission in the first imaging direction of the imaging module that is imaging the lesioned part when the lesioned part is detected.

The lesioned part detection unit 22 detects a lesioned part from image data output from the imaging module 4 or 6. The capsule control unit 21 may have a function of the lesioned part detection unit 22.

In addition, the capsule control unit 21 stores a program or necessary data for controlling the operation of the capsule control unit 21. A function of the capsule control unit 21, for example, can be implemented as a function of software by causing a computer of the capsule endoscope 20 to read and execute a program including a command for prescribing the operation of the capsule control unit 21. A method of installing the program may be similar to a method of installing a program for controlling the operation of the capsule control unit 8 of the capsule endoscope 1 according to the first embodiment.

In the reception apparatus 2 according to this embodiment, the lesion image storage unit 15 and the lesioned part detection unit 16 in the first embodiment are unnecessary.

In this embodiment, a difference from the first embodiment will be mainly described. Image data output from the imaging modules 4 and 6 are output to the lesioned part detection unit 22 through the capsule control unit 21. The lesioned part detection unit 22 performs the detection of the lesioned part such as bleeding which is relatively simpler than the detection of the lesioned part performed in the first embodiment and outputs a detection result to the capsule control unit 21. In the detection of the lesioned part performed by the lesioned part detection unit 22, lesion image data is not used.

The light emission motion instruction unit 23 of the capsule control unit 21 controls the light emission control unit 10 according to a detection result of the lesioned part and executes the normal light emission motion and the lesion light emission motion through a process similar to the light emission motion instruction process S1 in the first embodiment. Because the normal light emission motion and the lesion light emission motion are equivalent to those in the first embodiment, description thereof will be omitted. However, in the normal light emission motion instruction S5 and the lesion light emission motion instruction S7, the light emission motion instruction unit 23 instructs the light emission control unit 10 to perform the normal light emission motion or the lesion light emission motion in place of generating the instruction data.

In this embodiment, the image processing unit 13, the image accumulation unit 14, the lesion image storage unit 15, the lesioned part detection unit 16, and the reception apparatus control unit 17 are not essential components for obtaining a characteristic effect of the capsule endoscope system according to this embodiment.

According to this embodiment, a capsule endoscope system is configured to include: the capsule endoscope 20 having a first imaging module (imaging module 4 or 6) configured to direct an imaging direction in a first direction, image a first imaging range, and output first image data; a first light emission module (light emission module 3 or 5) configured to perform light emission in the first direction; a second imaging module (imaging module 4 or 6) configured to direct an imaging direction in a second direction different from the first direction in which the first imaging module performs imaging, image a second imaging range that does not overlap the first imaging range at a second timing different from a first timing at which the first imaging module performs imaging, and output second image data; a second light emission module (light emission module 3 or 5) configured to perform light emission in the second direction; the imaging control unit 9 configured to control the imaging of the first imaging module and the second imaging module; the light emission control unit 10 configured to control light emissions of the first light emission module and the second light emission module; and a first wireless communication interface (wireless communication unit 7) configured to transmit the first image data and the second image data; and the reception apparatus 2 having a second wireless communication interface (wireless communication unit 12) configured to receive the first image data and the second image data, wherein the capsule endoscope 20 has the lesioned part detection unit 22 configured to detect a lesioned part from the first image data or the second image data; and the light emission motion instruction unit 23 configured to instruct the light emission control unit 10 to execute a first light emission motion in which only a light emission module configured to perform the light emission in the imaging direction of an imaging module that is performing imaging performs the light emission when no lesioned part is detected and instruct the light emission control unit 10 to execute a second light emission motion in which a light emission module configured to perform the light emission in a second imaging direction of an imaging module different from an imaging module that is imaging the lesioned part performs the light emission in synchronization with the light emission by a light emission module configured to perform the light emission in the first imaging direction of the imaging module that is imaging the lesioned part when the lesioned part is detected.

According to this embodiment, the capsule endoscope 20 is configured to include a first imaging module (imaging module 4 or 6) configured to direct an imaging direction in a first direction, image a first imaging range, and output first image data; a first light emission module (light emission module 3 or 5) configured to perform light emission in the first direction; a second imaging module (imaging module 4 or 6) configured to direct an imaging direction in a second direction different from the first direction in which the first imaging module performs imaging, image a second imaging range that does not overlap the first imaging range at a second timing different from a first timing at which the first imaging module performs imaging, and output second image data; a second light emission module (light emission module 3 or 5) configured to perform light emission in the second direction; the imaging control unit 9 configured to control the imaging of the first imaging module and the second imaging module; the light emission control unit 10 configured to control light emissions of the first light emission module and the second light emission module; a wireless communication interface (wireless communication unit 7) configured to transmit the first image data and the second image data; the lesioned part detection unit 22 configured to detect a lesioned part from the first image data or the second image data; and the light emission motion instruction unit 23 configured to instruct the light emission control unit 10 to execute a first light emission motion in which only a light emission module configured to perform the light emission in the imaging direction of an imaging module that is performing imaging performs the light emission when no lesioned part is detected and instruct the light emission control unit 10 to execute a second light emission motion in which a light emission module configured to perform the light emission in a second imaging direction of an imaging module different from an imaging module that is imaging the lesioned part performs the light emission in synchronization with the light emission by a light emission module configured to perform the light emission in the first imaging direction of the imaging module that is imaging the lesioned part when the lesioned part is detected.

In addition, according to this embodiment, a light emission control method of the capsule endoscope is configured to include the step S3 of detecting a lesioned part from first image data or second image data generated by the capsule endoscope 20; and the steps S5 and S7 of instructing the light emission control unit 10 to execute a first light emission motion in which only a light emission module configured to perform the light emission in the imaging direction of an imaging module that is performing imaging performs the light emission when no lesioned part is detected and instructing the light emission control unit 10 to execute a second light emission motion in which a light emission module configured to perform the light emission in a second imaging direction of an imaging module different from an imaging module that is imaging the lesioned part performs the light emission in synchronization with the light emission by a light emission module configured to perform the light emission in the first imaging direction of the imaging module that is imaging the lesioned part when the lesioned part is detected.

In addition, according to this embodiment, a program is configured to cause a computer of the capsule endoscope 20 to execute the step S3 of detecting a lesioned part from first image data or second image data generated by the capsule endoscope 1; and the step of instructing the light emission control unit 10 to execute a first light emission motion in which only a light emission module configured to perform the light emission in the imaging direction of an imaging module that is performing imaging performs the light emission when no lesioned part is detected and instructing the light emission control unit 10 to execute a second light emission motion in which a light emission module configured to perform the light emission in a second imaging direction of an imaging module different from an imaging module that is imaging the lesioned part performs the light emission in synchronization with the light emission by a light emission module configured to perform the light emission in the first imaging direction of the imaging module that is imaging the lesioned part when the lesioned part is detected.

In this embodiment, it is possible to obtain a clearer image of a lesioned part by instructing the light emission control unit 10 to execute a first light emission motion, that is, the normal light emission motion, in which only the light emission module configured to perform the light emission in the imaging direction of an imaging module that is performing imaging performs the light emission when no lesioned part is detected and instructing the light emission control unit 10 to execute a second light emission motion, that is, the lesion light emission motion, in which a light emission module configured to perform the light emission in a second imaging direction of an imaging module different from an imaging module that is imaging the lesioned part performs the light emission in synchronization with the light emission by a light emission module configured to perform the light emission in the first imaging direction of the imaging module that is imaging the lesioned part when the lesioned part is detected.

Third Embodiment

Next, the third embodiment of the present invention will be described. This embodiment is an example in which a function of adjusting a light emission amount is added to the first embodiment. In this embodiment, the capsule endoscope 1 in the first embodiment is changed to a capsule endoscope 30 illustrated in FIG. 7.

Figure 7:
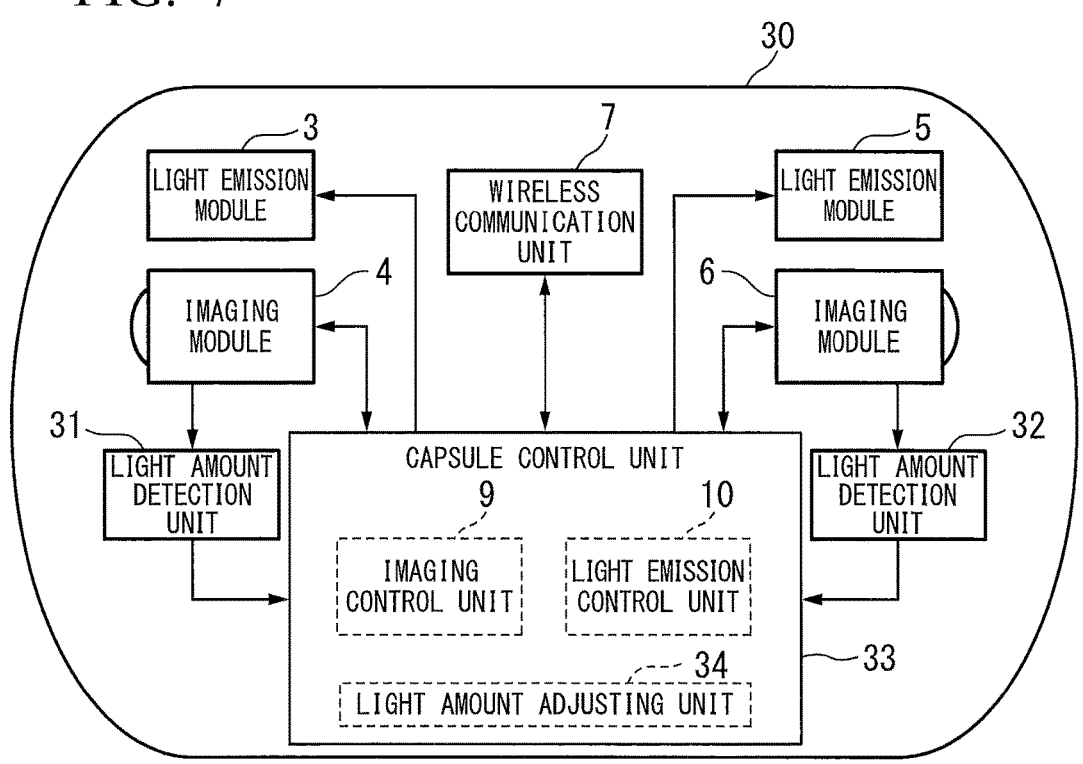
FIG. 7 is a block diagram illustrating a configuration example of a capsule endoscope according to a third embodiment of the present invention.

FIG. 7 illustrates a configuration example of the capsule endoscope 30. As illustrated in FIG. 7, the capsule endoscope 30 has a light emission module 3, an imaging module 4, a light emission module 5, an imaging module 6, a wireless communication unit 7, a light amount detecting unit 31, a light amount detecting unit 32, and a capsule control unit 33. In the capsule endoscope 30 of this embodiment, the capsule control unit 8 in the capsule endoscope 1 illustrated in FIG. 2 is changed to the capsule control unit 33 and the light amount detecting unit 31 and the light amount detecting unit 32 are added.

The light amount detecting unit 31 detects a light amount when the light emission module 3 or 5 performs the light emission based on a pixel signal read from the imaging module 4. The light amount detecting unit 32 detects a light amount when the light emission module 3 or 5 performs the light emission based on a pixel signal read from the imaging module 6. In this embodiment, the light amount is detected based on the image signal read from the imaging module 4 or 6 that is imaging the lesioned part.

The capsule control unit 33 has an imaging control unit 9, a light emission control unit 10, and a light amount adjusting unit 34. Because the imaging control unit 9 and the light emission control unit 10 have been described in the first embodiment, description thereof will be omitted. Based on the light intensities detected by the light amount detecting units 31 and 32, the light amount adjusting unit 34 adjusts the light intensities of the light emission modules 3 and 5 in the second light emission motion.

The imaging modules 4 and 6 have built-in complementary metal-oxide-semiconductor (CMOS) sensors. According to an amount of light incident on the CMOS sensor, it is possible to read a pixel signal accumulated in the pixel of the CMOS sensor in a non-destructive manner in the middle of imaging. Because the technology for reading the pixel signal from the CMOS sensor in the non-destructive manner is well known, description thereof will be omitted. The light amount detecting units 31 and 32 detect the light intensities as image luminances by reading the pixel signals from the imaging modules 4 and 6 that are performing imaging.

In this embodiment, a first light emission amount adjusting method and a second light emission amount adjusting method are possible. First, the first light emission amount adjusting method will be described.

A first light emission amount adjusting method is a method in which the light amount adjusting unit 34 adjusts the light intensities of the first light emission module 3 and the second light emission module 5 so that the light amount detected by the light amount detecting unit 31 or 32 becomes a preset target light amount when only the light emission module configured to perform the light emission in the second imaging direction of the imaging module different from the imaging module that is imaging the lesioned part performs the light emission in a second period subsequent to a first period after only the light emission module configured to perform the light emission in the first imaging direction of the imaging module that is imaging the lesioned part performs the light emission at a light amount lower than a light amount in the first light emission motion, that is, the normal light emission motion, in the first period of the first and second periods included in a period, that is, one frame period, in which the imaging module that is imaging the lesioned part performs the imaging.

For example, the case in which the light amount of the light emission module configured to perform the light emission in the first imaging direction of the imaging module that is imaging the lesioned part is a light amount corresponding to 70% of the light amount in the normal light emission motion, and the light amount of the light emission module configured to perform the light emission in the second imaging direction of the imaging module different from the imaging module that is imaging the lesioned part is a light amount corresponding to 30% of the light amount in the normal light emission motion will be described. Hereinafter, an example in which the imaging module 6 is imaging the lesioned part will be described. The light emission module 5 configured to perform the light emission in the first imaging direction of the imaging module 6 that is imaging the lesioned part is a light emission module of a lesion side, and the light emission module 3 configured to perform the light emission in the second imaging direction of the imaging module 4 different from the imaging module 6 that is imaging the lesioned part is a light emission module of an opposite side.

First, the light emission module 5 performs a light emission motion. The light amount detecting unit 32 sequentially detects the light amount in the state in which the light emission module 5 is emitting light from the pixel signal of the CMOS sensor within the imaging module 6. At a point in time at which the detected light amount has reached 70% of a target light amount in the normal light emission motion, the light amount adjusting unit 34 instructs the light emission control unit 10 to stop the light emission by the light emission module 5 and start the light emission by the light emission module 3. The light emission control unit 10 stops the light emission by the light emission module 5 and starts the light emission by the light emission module 3.

The light amount detecting unit 32 sequentially detects the light amount in a state in which the light emission module 3 is emitting light from the pixel signal of the CMOS sensor within the imaging module 6. At a point in time at which the light amount detected by the light amount detecting unit 32 has reached 100% of the target light amount in the normal light emission motion, the light amount adjusting unit 34 instructs the light emission control unit 10 to stop the light emission by the light emission module 3. The light emission control unit 10 stops the light emission by the light emission module 3. Through the above-described procedure, the light amount from the light emission module 5 becomes 70% and the light amount from the light emission module 3 becomes 30%. The above-described operation is performed in one frame period of the imaging module 6 that is imaging the lesioned part.

Figure 8:
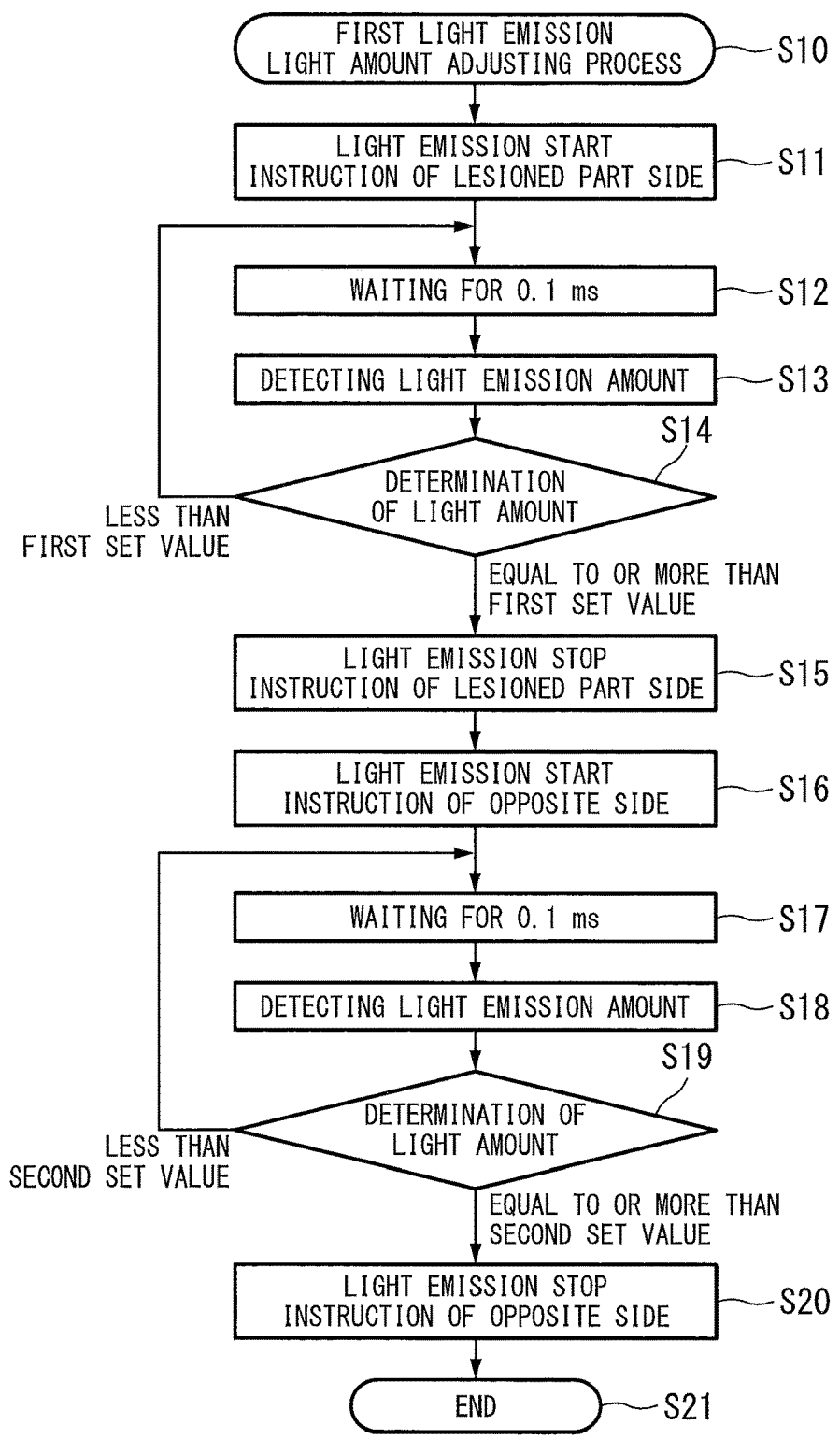
FIG. 8 is a flowchart illustrating a procedure of a first light emission amount adjusting process performed by the capsule endoscope according to the third embodiment of the present invention.

The first light emission amount adjusting method will be specifically described using FIG. 8. FIG. 8 illustrates a procedure of the first light emission amount adjusting process S10. The capsule control unit 33 performs the first light emission amount adjusting process S10 by controlling the light emission control unit 10 and the light amount adjusting unit 34.

The following process is performed in the first light emission amount adjusting process S10. In this example, the light amount detecting unit 32 configured to detect the light amount from the imaging module 6 that is imaging the lesioned part performs the detection of the light amount at intervals of 0.1 ms.

First, the light emission control unit 10 causes the light emission module of the lesion side to start the light emission motion according to a light emission start instruction S11 of the lesion side. As in the first embodiment, information indicating the imaging module that is imaging the lesioned part is included in instruction data transmitted from the reception apparatus 2. In a light emission start instruction S11 of the lesion side, the light emission control unit 10 causes the light emission module configured to perform the light emission in the imaging direction of the imaging module indicated by the information included in the instruction data to start the light emission motion. In the case of the above description, the light emission module 5 starts the light emission.

Subsequently, the light amount adjusting unit 34 waits for a predetermined time according to predetermined-time waiting S12. In this example, the predetermined time is 0.1 ms. When the predetermined time has elapsed, the light amount adjusting unit 34 performs light emission amount detection S13. The light emission amount detection S13 is a process of reading the light amount from the light amount detecting unit of the lesion side. Because the imaging module 6 images the lesioned part in the case of the above description, the light amount is read from the light amount detecting unit 32.

The light amount adjusting unit 34 determines whether the read light amount is greater than or equal to a first setting value according to a light amount determination S14. The first setting value is a value greater than 0 and is a value less than 100% of a preset target light amount. In the case of the above description, the first setting value is a value of 70% of the target light amount. When the light amount is less than the first setting value, the predetermined-time waiting S12 is performed. The process of S12 to S14 is iterated until the light amount is greater than or equal to the first setting value.

When the light amount is greater than or equal to the first setting value, the light amount adjusting unit 34 performs a light emission stop instruction S15 of the lesion side and a light emission start instruction S16 of the opposite side. The light emission stop instruction S15 of the lesion side is a process of causing the light emission control unit 10 to stop the light emission motion of the light emission module of the lesion side. The light emission start instruction S16 of the opposite side is a process of causing the light emission control unit 10 to start the light emission motion of the light emission module of the opposite side. In the case of the above description, the light emission module 5 stops the light emission and the light emission module 3 starts the light emission.

In the process of S11 to S15, the light amount adjusting unit 34 adjusts the light amount of the light emission module 5 so that the light amount detected by the light amount detecting unit 32 becomes a light amount lower than the preset target light amount when only the light emission module 5 configured to perform the light emission in the first imaging direction of the imaging module 6 that is imaging the lesioned part performs the light emission at a light amount lower than the light amount in the normal light emission motion in a first period of one frame period. In other words, according to the process of S11 to S15, the light amount adjusting unit 34 adjusts the light amount of the light emission module 5 so that the light amount detected by the light amount detecting unit 32 becomes a light amount lower than a preset target light amount when only the light emission module configured to perform the light emission in the first imaging direction of the imaging module that is imaging the lesioned part performs the light emission at a light amount lower than the light amount in the normal light emission motion in the first period.

After the light emission start instruction S16 of the opposite side, the light amount adjusting unit 34 waits for a predetermined time according to predetermined-time waiting S17. In this example, the predetermined time is 0.1 ms. When the predetermined time has elapsed, the light amount adjusting unit 34 performs light emission amount detection S18. The light emission amount detection S18 is a process of reading the light amount from the light amount detecting unit of the lesioned part. In the case of the above description, the light amount from the light amount detecting unit 32 is read because the imaging module 6 images the lesioned part.

The light amount adjusting unit 34 determines whether the read light amount is greater than or equal to a second setting value through a light amount determination S19. In the case of the above description, the second setting value is a value of 100% of the preset target light amount. When the light amount is less than the second setting value, the predetermined-time waiting S17 is performed. The process of S17 to S19 is iterated until the light amount is greater than or equal to the second setting value.

When the light amount is greater than or equal to the second setting value, the light amount adjusting unit 34 performs a light emission stop instruction S20 of the opposite side. The light emission stop instruction S20 of the opposite side is a process of causing the light emission control unit 10 to stop the light emission motion of the light emission module of the opposite side. In the case of the above description, the light emission module 3 stops the light emission. According to the process of S16 to S20, the light amount adjusting unit 34 adjusts the light amount of the light emission module 3 so that the light amount detected by the light amount detecting unit 32 becomes the target light amount when only the light emission module 3 configured to perform the light emission in the second imaging direction of the imaging module 4 different from the imaging module 6 that is imaging the lesioned part performs the light emission in the second period subsequent to the first period of one frame period.

In the case of the above description, the light emission stop instruction S20 of the opposite side is performed and the light emission module 3 ends the light emission at a point in time at which the light intensities of the light emission modules 5 and 3 have reached a value of 100% of the target light amount. When the above-described process is performed, the first light emission amount adjusting process S10 ends (S21).

In the above description, the light amount of the light emission module of the lesion side is detected (S13). On the other hand, after the light emission module of the lesion side performs the light emission for a preset time (for example, a time of 50% of a light emission time in the normal light emission motion) shorter than a light emission time in the normal light emission motion of the light emission module of the lesion side, the light emission module of the lesion side may stop the light emission. Accordingly, in the first light emission amount adjusting method, the light emission amount detection S13 and the light amount determination S14 are not essential.

Next, a second light emission amount adjusting method will be described. The second light emission amount adjusting method is a method in which the light amount adjusting unit 34 adjusts the light intensities of the first light emission module 3 and the second light emission module 5 so that the light amount detected by the light amount detecting unit 31 or 32 becomes a preset target light amount when only the light emission module configured to perform the light emission in the first imaging direction performs the light emission in a second period subsequent to a first period after only the light emission module configured to perform the light emission in the second imaging direction of the image module different from the imaging module that is imaging the lesioned part performs the light emission at a light amount equal to a light amount in the normal light emission motion in the first period of the first and second periods included in a period, that is, one frame period, in which the imaging module that is imaging the lesioned part performs the imaging.

For example, the case in which the light amount of the light emission module configured to perform the light emission in the second imaging direction of the imaging module different from an imaging module that is imaging the lesioned part is a light amount corresponding to 50% of the light amount in the normal light emission motion and the light amount of the light emission module configured to perform the light emission in the first imaging direction of the imaging module that is imaging the lesioned part is a light amount corresponding to 50% of the light amount in the normal light emission motion will be described. Hereinafter, an example in which the imaging module 6 is imaging the lesioned part will be described. The light emission module 5 configured to perform the light emission in the first imaging direction of the imaging module 6 that is imaging the lesioned part is the light emission module of the lesion side and the light emission module 3 configured to perform the light emission in the second imaging direction of the imaging module 4 different from the imaging module 6 that is imaging the lesioned part is a light emission module of the opposite side.

First, the light emission module 3 performs a light emission motion. At a point in time at which it is estimated that the light amount of the light emission module 3 has reached 50% of the target light amount in the normal light emission motion, the light amount adjusting unit 34 instructs the light emission control unit 10 to stop the light emission by the light emission module 3 and start the light emission by the light emission module 5. The light emission control unit 10 stops the light emission by the light emission module 3 and starts the light emission by the light emission module 5.

The light amount detecting unit 32 sequentially detects the light amount in a state in which the light emission module 5 is emitting light from a pixel signal of the CMOS sensor within the imaging module 6. At a point in time at which the light amount detected by the light amount detecting unit 32 has reached 100% of a target light amount in the normal light emission motion, the light amount adjusting unit 34 instructs the light emission control unit 10 to stop the light emission by the light emission module 5. The light emission control unit 10 stops the light emission by the light emission module 5. Through the above-described procedure, the light amount from the light emission module 3 becomes 50% and the light amount from the light emission module 5 becomes 50%. The above-described operation is performed in one frame period of the imaging module 6 that is imaging the lesioned part.

Figure 9:
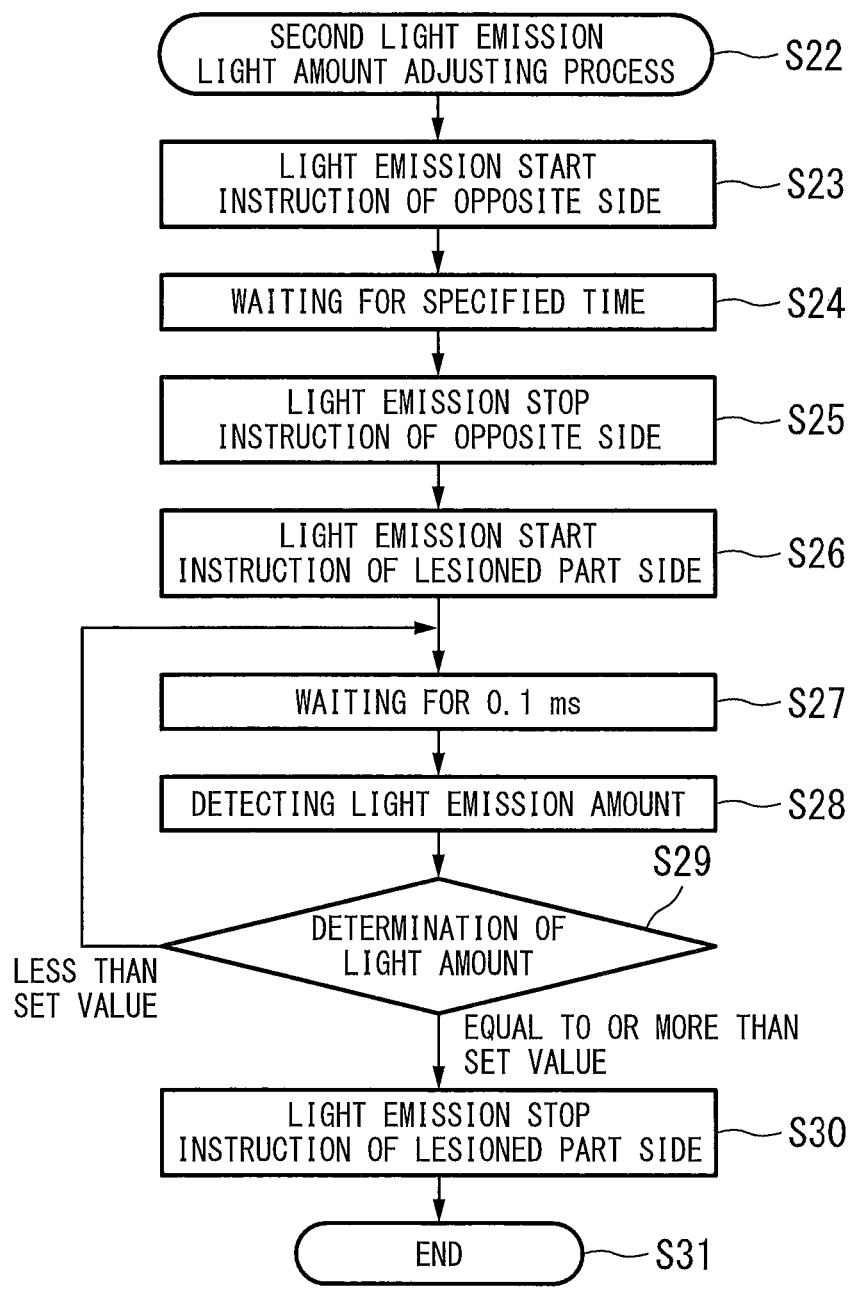
FIG. 9 is a flowchart illustrating a procedure of a second light emission amount adjusting process performed by the capsule endoscope according to the third embodiment of the present invention.

The second light emission amount adjusting method will be specifically described using FIG. 9. FIG. 9 illustrates the procedure of a second light emission amount adjusting process S22. The capsule control unit 33 performs the second light emission amount adjusting process S22 by controlling the light emission control unit 10 and the light amount adjusting unit 34.

In the second light emission amount adjusting process S22, the following process is performed. In this example, the light amount detecting unit 32 configured to detect the light amount from the imaging module 6 that is imaging the lesioned part performs the detection of the light amount at intervals of 0.1 ms.

First, the light emission control unit 10 causes the light emission module of the opposite side to start the light emission motion according to a light emission start instruction S23 of the opposite side. As in the first embodiment, information indicating the imaging module that is imaging the lesioned part is included in instruction data transmitted from the reception apparatus 2. In the light emission start instruction S23 of the opposite side, the light emission control unit 10 causes the light emission module configured to perform the light emission in the imaging direction of the imaging module different from the imaging module indicated by the information included in the instruction data to start the light emission motion. In the case of the above description, the light emission module 3 starts the light emission.

Subsequently, the light amount adjusting unit 34 waits for a prescribed time according to prescribed-time waiting S24. In this example, the prescribed time is 2 ms. The prescribed time, for example, is a time equal to a light emission time in the immediately previously performed normal light emission motion. When the illumination by reflected light is performed at an efficiency of 50% of the illumination by the direct light, the light amount by the light emission of the prescribed time becomes 50% of the target light amount in the normal light emission motion.

When the prescribed time has elapsed, the light amount adjusting unit 34 performs a light emission stop instruction S25 of the opposite side and a light emission start instruction S26 of the lesion side. The light emission stop instruction S25 of the opposite side is a process of causing the light emission control unit 10 to stop the light emission motion of the light emission module of the opposite side. The light emission start instruction S26 of the lesion side is a process of causing the light emission control unit 10 to start the light emission motion of the light emission module of the lesion side. In the case of the above description, the light emission module 3 stops the light emission and the light emission module 5 starts the light emission.

According to the process of S23 to S25, the light amount adjusting unit 34 adjusts the light amount of the light emission module 3 so that only the light emission module 3 configured to perform the light emission in the second imaging direction of the imaging module 4 different from the imaging module 6 that is imaging the lesioned part performs the light emission at the same light amount as the light amount in the normal light emission motion in the first period of one frame period.

Subsequently, the light amount adjusting unit 34 waits for a predetermined time according to predetermined-time waiting S27. In this example, the predetermined time is 0.1 ms. When the predetermined time has elapsed, the light amount adjusting unit 34 performs light emission amount detection S28. The light emission amount detection S28 is a process of reading the light amount from the light amount detecting unit of the lesion side. In the case of the above description, the light amount from the light amount detecting unit 32 is read because the imaging module 6 images the lesioned part.

The light amount adjusting unit 34 determines whether the read light amount is greater than or equal to a setting value through a light amount determination S29. In the case of the above description, the setting value is a value of 100% of the preset target light amount. When the light amount is less than the setting value, the predetermined-time waiting S27 is performed. The process of S27 to S29 is iterated until the light amount is greater than or equal to the setting value.

When the light amount is greater than or equal to the setting value, the light amount adjusting unit 34 performs a light emission stop instruction S30 of the lesion side. The light emission stop instruction S30 of the lesion side is a process of causing the light emission control unit 10 to stop the light emission motion of the light emission module of the lesion side. In the case of the above description, the light emission module 5 stops the light emission. According to the process of S27 to S30, the light amount adjusting unit 34 adjusts the light amount of the light emission module 5 so that the light amount detected by the light amount detecting unit 32 becomes the target light amount when only the light emission module 5 configured to perform the light emission in the first imaging direction of the imaging module 6 that is imaging the lesioned part performs the light emission in the second period subsequent to the first period of one frame period.

In the case of the above description, the light emission stop instruction S30 of the lesion side is performed and the light emission module 5 ends the light emission at a point in time at which the light intensities of the light emission modules 3 and 5 have reached a value of 100% of the target light amount. When the above-described process is performed, the second light emission amount adjusting process S22 ends (S31).

In the above description, after prescribed-time waiting S24, a light emission start instruction S26 of the lesion side is performed. On the other hand, the light emission module of the opposite side performs the light emission, and the light emission module of the opposite side may stop the light emission when the light amount detected by the light amount detecting unit from the imaging module that is imaging the lesioned part has reached a predetermined light amount lower than the target light amount. That is, in the first period, the light amount adjusting unit 34 may adjust the light amount of the light emission module so that the light amount detected by the light amount detecting unit becomes a light amount lower than the preset target light amount when only the light emission module configured to perform the light emission in the second imaging direction of the imaging module different from an imaging module that is imaging the lesioned part performs the light emission. Accordingly, in the second light emission amount adjusting method, the prescribed-time waiting S24 is not essential.

In this embodiment, the image processing unit 13 and the image accumulation unit 14 are not essential components for obtaining a characteristic effect of the capsule endoscope system according to this embodiment. In addition, the lesion image storage unit 15 is not an essential component in the capsule endoscope system according to this embodiment.

In this embodiment, it is possible to perform imaging by adjusting light emission intensities of the light emission modules 3 and 5 during the lesion light emission motion in either of the first and second light emission amount adjusting methods. In addition, at the time of imaging of the lesioned part, the first and second light emission amount adjusting methods and the light emission method of a normal imaging time are sequentially switched and performed, so that imaging in various illumination states is possible and detailed observation of the lesioned part is possible.

Fourth Embodiment

Next, the fourth embodiment of the present invention will be described. This embodiment is an example in which a normal light emission motion, as well as a lesion light emission motion, is executable as the illumination method of the imaging time of the lesioned part. In this embodiment, the reception apparatus 2 in the first embodiment is changed to a reception apparatus 40 illustrated in FIG. 10.

Figure 10:
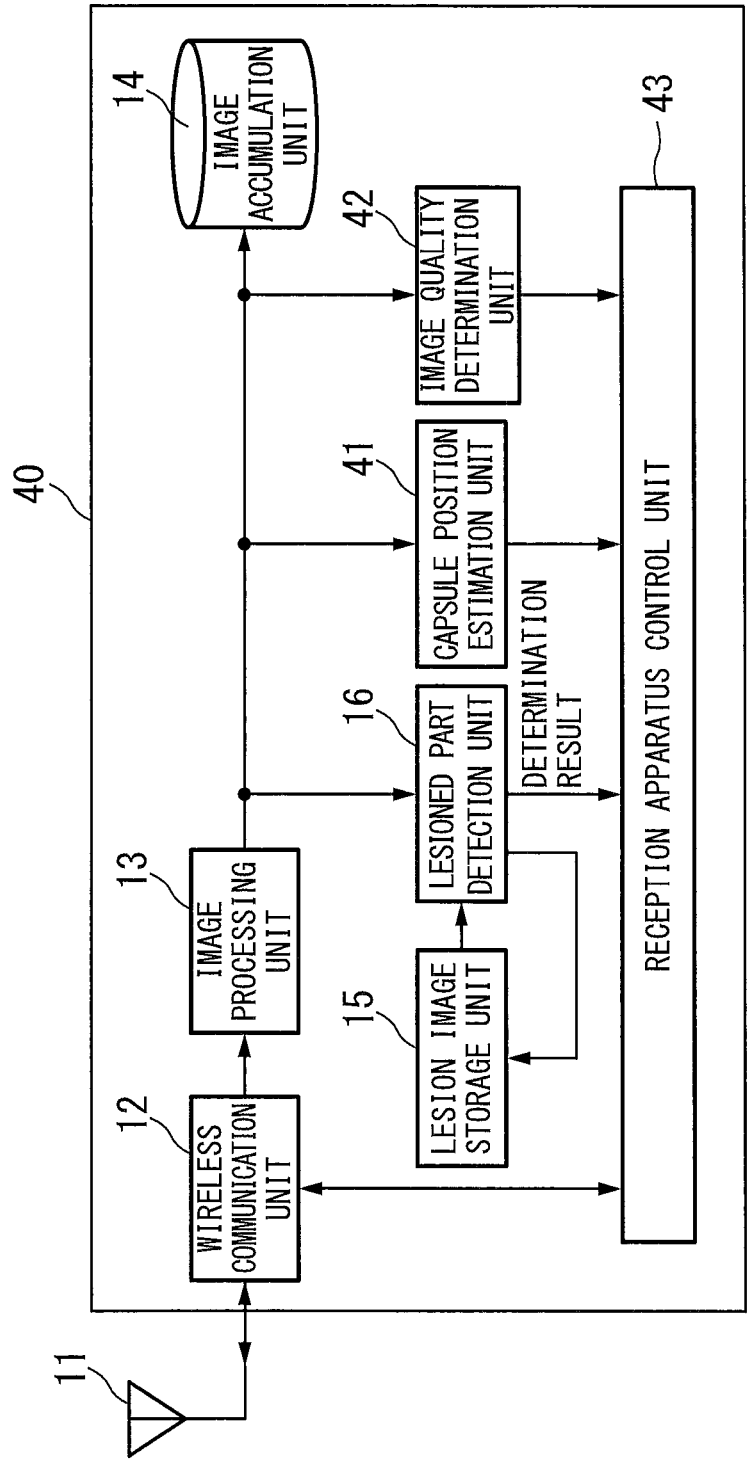
FIG. 10 is a block diagram illustrating a configuration example of a reception apparatus according to a fourth embodiment of the present invention.

FIG. 10 illustrates a configuration example of the reception apparatus 40. As illustrated in FIG. 10, the reception apparatus 40 has an antenna 11, a wireless communication unit 12, an image processing unit 13, an image accumulation unit 14, a lesion image storage unit 15, a lesioned part detection unit 16, a capsule position estimating unit 41, an image quality determination unit 42, and a reception apparatus control unit 43.

In the reception apparatus 40 of this embodiment, the reception apparatus control unit 17 in the reception apparatus 2 illustrated in FIG. 3 is changed to the reception apparatus control unit 43 and the capsule position estimating unit 41 and the image quality determination unit 42 are added.

Image data processed by the image processing unit 13 is output to the image accumulation unit 14, the lesioned part detection unit 16, the capsule position estimating unit 41, and the image quality determination unit 42. The capsule position estimating unit 41 estimates a position of the capsule endoscope 1, that is, a type of organ through which the capsule endoscope 1 is passing, based on the image data. Because an algorithm of estimating the position of the capsule endoscope from the image data is well known, description thereof will be omitted.

The image quality determination unit 42 determines image data having higher image quality than other image data by comparing data of two images output from the same imaging module. In this embodiment, the image quality determination unit 42 determines that image data having a relatively wide distribution in a histogram has good image quality by comparing histograms of image data at the time of imaging the lesioned part when the lesion light emission motion is performed and image data at the time of imaging the lesioned part when the normal light emission motion is performed. The histogram indicates the number of pixels for every received light amount. For example, the horizontal axis of the histogram represents a received light amount and the vertical axis of the histogram represents the number of pixels.

As an illumination method when the lesioned part is imaged in this embodiment, methods of the following (1) to (3) can be selected.

(1) A method in which the lesion light emission motion is performed only when a position estimated by the capsule position estimating unit 41 is within a predetermined organ and only the normal light emission motion is performed even when the lesioned part is detected when the position estimated by the capsule position estimating unit 41 is within another organ.

(2) A method of alternately performing the normal light emission motion and the lesion light emission motion during the imaging of the lesioned part.

(3) A method of determining image qualities of image data when the normal light emission motion is performed immediately before the lesioned part is detected and image data when the lesion light emission motion is performed immediately after the lesioned part is detected when the lesioned part is first detected and continuing imaging of the lesioned part using the light emission motion used in imaging related to image data determined to have relatively good image quality.

In the method of (1), the reception apparatus control unit 43 determines whether to execute the lesion light emission motion according to a type of organ which is being imaged by the capsule endoscope 1.

In the method of (2), the reception apparatus control unit 43 instructs the light emission control unit 10 to alternately execute the first light emission motion, that is, the normal light emission motion, and the second light emission motion, that is, the lesion light emission motion, when the lesioned part has been detected.

In the method of (3), after instructing the light emission control unit 10 to execute the first light emission motion, that is, the normal light emission motion, when no lesioned part is detected, the reception apparatus control unit 43 instructs the light emission control unit 10 to execute the second light emission motion, that is, the lesion light emission motion, when the lesioned part is detected and instructs the light emission control unit 10 to execute the normal light emission motion or the lesion light emission motion used in imaging according to image data determined to have higher image quality than other image data by the image quality determination unit 42 comparing image data output when the light emission is performed in the normal light emission motion to image data output when the light emission is performed in the lesion light emission motion.

Characteristics of the methods of (1) to (3) are as follows. In the method of (1), it is possible to stop the lesion light emission motion in an organ inappropriate for the lesion light emission motion. Specifically, no lesion light emission motion is performed when the capsule endoscope 1 is located in a stomach and a small intestine. In many cases, the reflected light is not radiated to the lesioned part because the inside of the tube in the small intestine is too narrow. In contrast, the reflected light is not radiated to the lesioned part because the inside of the stomach is too wide. Because power is ineffectively consumed even when the lesion light emission motion is performed in these organs, no lesion light emission motion is performed.

In the method of (2), it is possible to acquire both image data when the illumination state is varied from the normal state and only the lesioned part is imaged and image data when the lesioned part and a part other than the lesioned part are imaged in the normal illumination state. Thereby, it is possible to maintain continuity of imaging of the overall organ including the lesioned part and acquire an image of the lesioned part obtained by varying the illumination state.

In the method of (3), it is possible to perform the illumination of the lesioned part having a shape more appropriate for imaging in the normal light emission motion when the illumination is performed in the normal light emission motion rather than when the illumination is performed in the lesion light emission motion.

Figure 11:
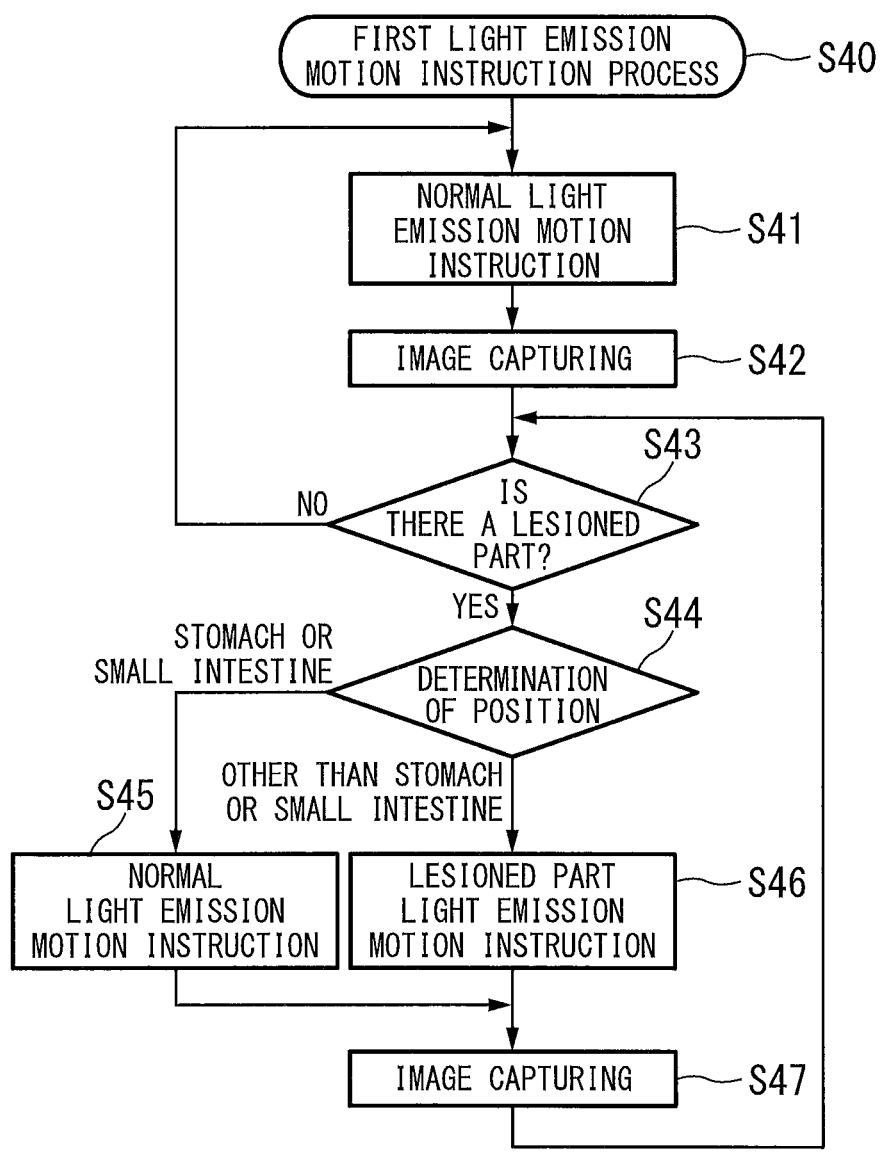
FIG. 11 is a flowchart illustrating a procedure of a first light emission motion instruction process performed by the reception apparatus according to the fourth embodiment of the present invention.

Next, a procedure of performing light emission in the methods of the above-described (1) to (3) will be described using FIGS. 11 to 13. FIG. 11 illustrates a procedure of a first light emission motion instruction process S40 corresponding to the method of (1).

In the first light emission motion instruction process S40, the following process is performed. First, the reception apparatus control unit 43 performs a normal light emission motion instruction S41 for instructing the capsule endoscope 1 to perform the normal light emission motion. In the normal light emission motion instruction S41, the reception apparatus control unit 43 generates instruction data indicating an instruction of the normal light emission motion and transmits the instruction data from the wireless communication unit 12 to the capsule endoscope 1. The capsule control unit 8 of the capsule endoscope 1 instructs the light emission control unit 10 to execute the normal light emission motion based on instruction data received by the wireless communication unit 7. The light emission control unit 10 causes the light emission modules 3 and 5 to start the normal light emission motion.

After the normal light emission motion instruction S41, the lesioned part detection unit 16 fetches image data output from the image processing unit 13 and the lesion image data stored in the lesion image storage unit 15 through image fetching S42. The lesioned part detection unit 16 compares the fetched image data and determines whether there is a lesioned part in the image data output from the image processing unit 13 (S43). The reception apparatus control unit 43 is notified of a result of the determination made by the lesioned part detection unit 16.

When it is determined that there is no lesioned part, the normal light emission motion instruction S41 is performed. When it is determined that the lesioned part is present, the capsule position estimating unit 41 makes a position determination S44 for determining the position of the capsule endoscope 1 based on image data output from the image processing unit 13. When the position of the capsule endoscope 1 is a stomach or a small intestine, the reception apparatus control unit 43 performs a normal light emission motion instruction S45 for instructing the capsule endoscope 1 to perform the normal light emission motion. Because the normal light emission motion instruction 45 is a process similar to the normal light emission motion instruction S41, description thereof will be omitted.

When the position of the capsule endoscope 1 is an organ other than the stomach and the small intestine, the reception apparatus control unit 43 performs a lesion light emission motion instruction S46 for instructing the capsule endoscope 1 to perform the lesion light emission motion. In the lesion light emission motion instruction S46, the reception apparatus control unit 43 generates instruction data indicating an instruction of the lesion light emission motion and transmits the instruction data from the wireless communication unit 12 to the capsule endoscope 1. In the instruction data, information indicating the imaging module outputting the image data from which the lesioned part is detected, that is, the imaging module that is imaging the lesioned part, is included. The capsule control unit 8 of the capsule endoscope 1 instructs the light emission control unit 10 to execute the lesion light emission motion based on the instruction data received by the wireless communication unit 7. The light emission control unit 10 causes the light emission modules 3 and 5 to perform the lesion light emission motion in which the other light emission module performs the light emission in synchronization with the light emission by a light emission module configured to perform the light emission in the imaging direction of the imaging module indicated by the information included in the instruction data.

After the normal light emission motion instruction S45 or the lesion light emission motion instruction S46, image fetching S47 is performed. Because the image fetching S47 is a process similar to the image fetching S42, description thereof will be omitted. After the image fetching S47, a determination S43 of whether there is a lesioned part in the image data is made. Through the above-described process, a light emission motion selected according to the position of the lesioned part is executed.

Figure 12:
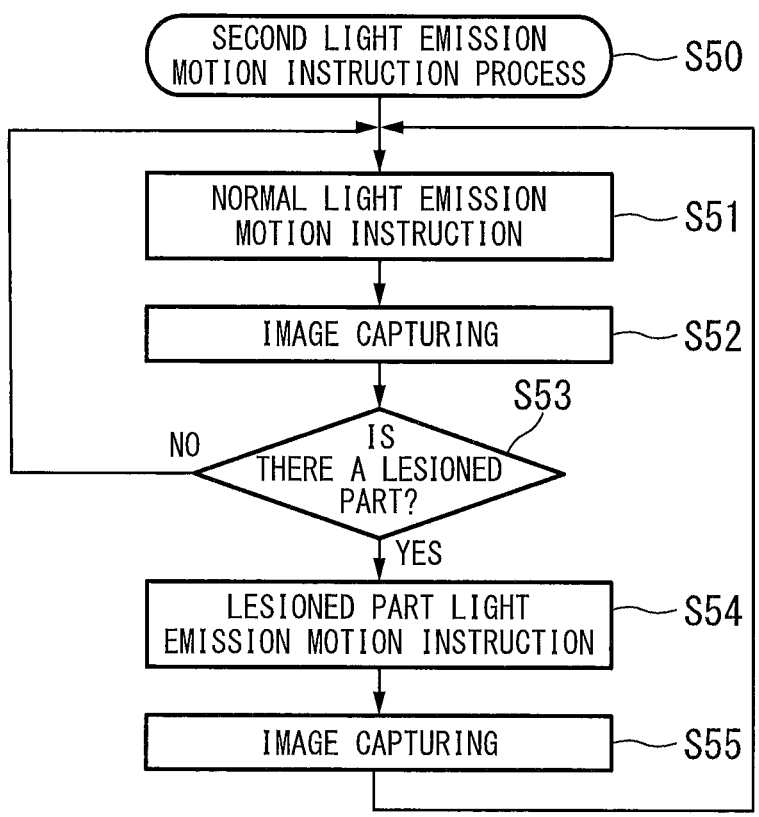
FIG. 12 is a flowchart illustrating a procedure of a second light emission motion instruction process performed by the reception apparatus according to the fourth embodiment of the present invention.

FIG. 12 illustrates a procedure of a second light emission motion instruction process S50 corresponding to the method of (2). In the second light emission motion instruction process S50, as in the first light emission motion instruction process S40, a normal light emission motion instruction S51 and image fetching S52 are iteratively performed until the lesioned part is detected. Because the normal light emission motion instruction S51 is a process similar to the normal light emission motion instruction S41, description thereof will be omitted. Because the image fetching S52 is a process similar to the image fetching S42, description thereof will be omitted.

After the image fetching S52, the lesioned part detection unit 16 compares the fetched image data and determines whether there is a lesioned part in image data output from the image processing unit 13 (S53). When it is determined that there is no lesioned part, the normal light emission motion instruction S51 is performed. When it is determined that there is a lesioned part, a lesion light emission motion instruction S54 is performed. Because the lesion light emission motion instruction S54 is a process similar to the lesion light emission motion instruction S46, description thereof will be omitted.

After the lesion light emission motion instruction S54, image fetching S55 is performed. Because the image fetching S55 is a process similar to the image fetching S42, description thereof will be omitted. After the image fetching S55, the normal light emission motion instruction S51 is performed. During a period in which the lesioned part is imaged through the above-described process, the normal light emission motion instruction S51 and the lesion light emission motion instruction S54 are iteratively performed.

When the lesioned part is detected, the normal light emission motion instruction S51 and the lesion light emission motion instruction S54 are performed for every period in which the imaging module that is imaging the lesioned part performs imaging. That is, in one frame period in which the imaging module that is imaging the lesioned part performs imaging, either of the normal light emission motion instruction S51 and the lesion light emission motion instruction S54 is performed. For example, the imaging module that is imaging the lesioned part performs the imaging and the lesion light emission motion instruction S54 is performed in a certain frame period, and the imaging module that is imaging the lesioned part performs imaging and the normal light emission motion instruction S51 is performed in the next frame period after the frame period.

Figure 13:
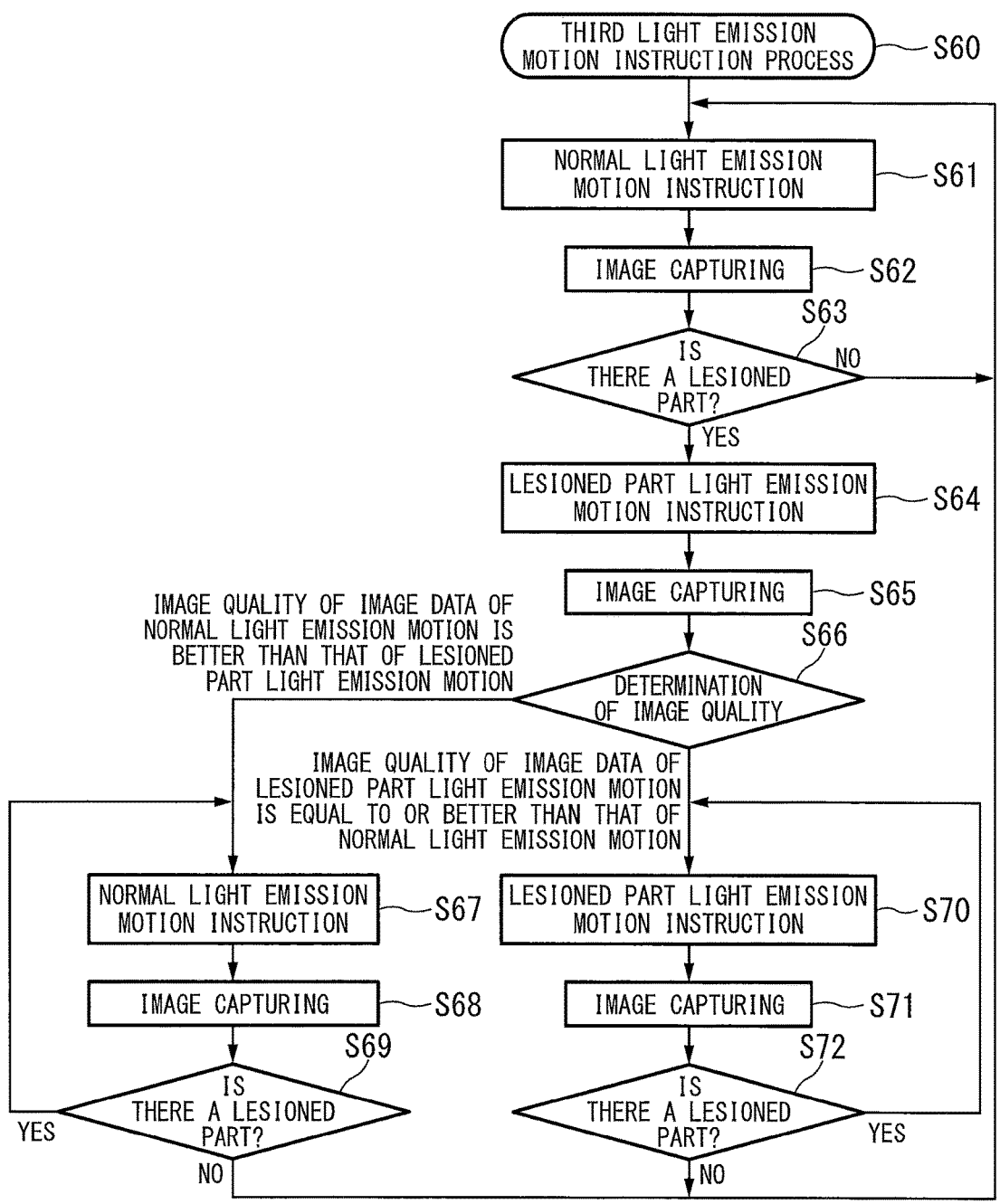
FIG. 13 is a flowchart illustrating a procedure of a third light emission motion instruction process performed by the reception apparatus according to the fourth embodiment of the present invention.

FIG. 13 illustrates a procedure of a third light emission motion instruction process S60 corresponding to the method of (3). In the third light emission motion instruction process S60, as in the first light emission motion instruction process S40, a normal light emission motion instruction S61 and image fetching S62 are iteratively performed until the lesioned part is detected. Because the normal light emission motion instruction S61 is a process similar to the normal light emission motion instruction S41, description thereof will be omitted. In the image fetching S62, the lesioned part detection unit 16 fetches image data output from the image processing unit 13 and image data stored in the lesion image storage unit 15 and the image quality determination unit 42 fetches the image data output from the image processing unit 13.

After the image fetching S62, the lesioned part detection unit 16 compares the fetched image data and determines whether there is a lesioned part in the image data output from the image processing unit 13 (S63). When it is determined that there is no lesioned part, the normal light emission motion instruction S61 is performed. When it is determined that the lesioned part is present, a lesion light emission motion instruction S64 is performed. Because the lesion light emission motion instruction S64 is a process similar to the lesion light emission motion instruction S46, description thereof will be omitted.

After the lesion light emission motion instruction S64, the image quality determination unit 42 fetches image data output from the image processing unit 13 through image fetching S65. After the image fetching S65, the image quality determination unit 42 compares image data fetched in the image fetching S62 after the immediately previous normal light emission motion instruction S61 to image data fetched in the image fetching S65 after the immediately previous lesion light emission motion instruction S64, and performs an image quality determination S66 for determining image quality. The reception apparatus control unit 43 is notified of a determination result.

When it is determined that the image data fetched in the image fetching S62 after the normal light emission motion instruction S61 has higher image quality than the image data fetched in the image fetching S65 after the lesion light emission motion instruction S64, a normal light emission motion instruction S67 is performed. Because the normal light emission motion instruction S67 is a process similar to the normal light emission motion instruction S41, description thereof will be omitted. After the normal light emission motion instruction S67, image fetching S68 is performed. Because the image fetching S68 is a process similar to the image fetching S62, description thereof will be omitted.

After the image fetching S68, the lesioned part detection unit 16 compares the fetched image data and determines whether there is a lesioned part in the image data output from the image processing unit 13 (S69). When it is determined that there is a lesioned part, the normal light emission motion instruction S67 is performed. Accordingly, the normal light emission motion instruction S67 and the image fetching S68 are continuously performed until the imaging of the lesioned part being imaged ends. When it is determined that there is no lesioned part, the normal light emission motion instruction S61 is performed.

When it is determined that the image data fetched in the image fetching S65 after the lesion light emission motion instruction S64 has higher image quality than the image data fetched in the image fetching S62 after the normal light emission motion instruction S61 or when it is determined that both image qualities of the image data are comparable, a lesion light emission motion instruction S70 is performed. Because the lesion light emission motion instruction S70 is a process similar to the lesion light emission motion instruction S46, description thereof will be omitted. After the lesion light emission motion instruction S70, image fetching S71 is performed. Because the image fetching S71 is a process similar to the image fetching S62, description thereof will be omitted.

After the image fetching S71, the lesioned part detection unit 16 compares the fetched image data and determines whether there is a lesioned part in the image data output from the image processing unit 13 (S72). When it is determined that there is a lesioned part, the lesion light emission motion instruction S70 is performed. Accordingly, the lesion light emission motion instruction S70 and the image fetching S71 are continuously performed until the imaging of the lesioned part being imaged ends. When it is determined that there is no lesioned part, the normal light emission motion instruction S61 is performed. Through the above-described process, the light emission motion selected according to the image quality determination S66 is executed during a period in which the lesioned part is imaged.

Although the present invention is compatible with the methods of (1) to (3) in this embodiment, the present invention may be compatible with only one or two of the methods of (1) to (3). In addition, when the present invention is compatible with only one or two of the methods of (1) to (3), a component related to a process that is not executed in the reception apparatus is unnecessary. For example, when the reception apparatus compatible with only the method of (1) is configured, the image quality determination unit 42 is unnecessary. In addition, when the reception apparatus compatible with only the method of (3) is configured, the capsule position estimating unit 41 is unnecessary.

In this embodiment, the image processing unit 13 and the image accumulation unit 14 are not essential components for obtaining a characteristic effect of the capsule endoscope system according to this embodiment. In addition, the lesion image storage unit 15 is not an essential component in the capsule endoscope system according to this embodiment.

In this embodiment, it is possible to stop the lesion light emission motion in an organ inappropriate for the lesion light emission motion through the method of (1). In addition, through the method of (2), it is possible to maintain continuity of imaging of the overall organ including the lesioned part and acquire an image of the lesioned part obtained by varying the illumination state. In addition, through the method of (3), it is possible to perform the illumination of the lesioned part having a shape more appropriate for imaging in the normal light emission motion when the illumination is performed in the normal light emission motion rather than when the illumination is performed in the lesion light emission motion.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A capsule endoscope system comprising:
   a capsule endoscope having:
   a first image sensor configured to capture an image in a first direction in a first imaging area, and output first image data;
   a first light source configured to perform light emission in the first direction;
   a second image sensor configured to capture an image in a second direction different from the first direction in a second imaging area that does not overlap the first imaging area at a second time different from a first time at which the first image sensor performs imaging, and output second image data;
   a second light source configured to perform light emission in the second direction;
   an imaging controller configured to control the imaging by the first image sensor and the second image sensor;
   the imaging controller further being configured to control light emissions by the first light source and the second light source; and
   a first wireless communication interface configured to transmit the first image data and the second image data; and
   a receiver having a second wireless communication interface configured to receive the first image data and the second image data,
   wherein the capsule endoscope or the reception apparatus is configured to detect a lesioned part from the first image data or the second image data; and
   a controller configured to instruct the imaging controller to execute a first light emission operation in which only a light source configured to perform the light emission in the imaging direction of an image sensor that is performing imaging performs the light emission when no lesioned part is detected and instruct the imaging controller to execute a second light emission operation in which a light source configured to perform the light emission in a second imaging direction of an image sensor different from an image sensor that is imaging the lesioned part performs the light emission in synchronization with the light emission by a light source configured to perform the light emission in a first imaging direction of the image sensor that is imaging the lesioned part when the lesioned part is detected.

2. The capsule endoscope system according to claim 1, wherein the reception apparatus is configured to detect the lesioned part from the the first image data or the second image data and comprises:
   the controller;
   wherein the controller is further configured to detect the light amount when the first light source or the second light source performs the light emission from a pixel signal accumulated in the image sensor that is imaging the lesioned part; and
   to adjust light intensities of the first light source and the second light source in the second light emission operation based on the light amount detected by the light amount detecting unit, and wherein the controller adjusts the light intensities of the first light source and the second light source so that the light amount detected becomes a preset target light amount when only the light source configured to perform the light emission in the second imaging direction performs the light emission in a second period subsequent to a first period after only the light source configured to perform the light emission in the first imaging direction performs the light emission at a light amount lower than a light amount in the first light emission operation in the first period of the first and second periods included in a period in which the image sensor that is imaging the lesioned part performs the imaging.

3. The capsule endoscope system according to claim 1, wherein the reception apparatus is configured to detect the lesioned part from the the first image data or the second image data and comprises:
the controller;
wherein the controller is further configured to detect the light amount when the first light source or the second light source performs the light emission from a pixel signal accumulated in the image sensor that is imaging the lesioned part; and
to adjust light intensities of the first light source and the second light source in the second light emission operation based on the light amount detected by the light amount detecting unit, and
wherein the controller adjusts the light intensities of the first light source and the second light source so that the light amount detected becomes a preset target light amount when only the light source configured to perform the light emission in the first imaging direction performs the light emission in a second period subsequent to a first period after only the light source configured to perform the light emission in the second imaging direction performs the light emission at a light amount equal to a light amount in the first light emission operation in the first period of the first and second periods included in a period in which the image sensor that is imaging the lesioned part performs the imaging.

4. The capsule endoscope system according to claim 1, wherein the controller determines whether to execute the second light emission operation according to a type of organ being imaged by the capsule endoscope.

5. The capsule endoscope system according to claim 1, wherein the controller instructs the light emission control unit to alternately execute the first light emission operation and the second light emission operation when the lesioned part is detected.

6. The capsule endoscope system according to claim 1, wherein the reception apparatus is configured to detect the lesioned part from the the first image data or the second image data and comprises:
the controller;
wherein the controller is configured to determine image data having image quality higher than image quality of other image data by comparing data of two images output from the same image sensor,
wherein the controller instructs the imaging controller to execute the second light emission operation when the lesioned part is detected after instructing the imaging controller to execute the first light emission operation when no lesioned part is detected and instructs the light emission control unit to execute the first light emission operation or the second light emission operation used in the imaging related to the image data determined to have the image quality higher than the image quality of the other image data by comparing image data output when the light emission is performed in the first light emission operation to image data output when the light emission is performed in the second light emission operation.

7. A reception apparatus comprising:
a second wireless communication interface configured to receive first image data and second image data from a capsule endoscope having:
a first image sensor configured to direct an imaging direction in a first direction, image a first imaging range, and output the first image data;
a first light source configured to perform light emission in the first direction;
a second image sensor configured to direct an imaging direction in a second direction different from the first direction, image a second imaging range that does not overlap the first imaging range at a second timing different from a first timing at which the first image sensor performs imaging, and output second image data;
a second light source configured to perform light emission in the second direction;
an imaging controller configured to control the imaging of the first image sensor and the second image sensor;
the imaging controller further being configured to control light emissions of the first light source and the second light source; and
a first wireless communication interface configured to transmit the first image data and the second image data;
a controller configured to detect a lesioned part from the first image data or the second image data, and
to transmit instruction data for instructing the imaging controller to execute a first light emission operation in which only a light source configured to perform the light emission in the imaging direction of an image sensor that is performing imaging performs the light emission when no lesioned part is detected and instructing the imaging controller to execute a second light emission operation in which a light source configured to perform the light emission in a second imaging direction of an image sensor different from an image sensor that is imaging the lesioned part performs the light emission in synchronization with the light emission by a light source configured to perform the light emission in a first imaging direction of the image sensor that is imaging the lesioned part when the lesioned part is detected from the second wireless communication interface to the capsule endoscope.

* * * * *